(12) United States Patent
Hiraguchi

(10) Patent No.: US 12,115,499 B2
(45) Date of Patent: Oct. 15, 2024

(54) OXYGENATOR AND METHOD FOR MANUFACTURING THE SAME

(71) Applicant: TERUMO KABUSHIKI KAISHA, Tokyo (JP)

(72) Inventor: Ryuji Hiraguchi, Elkton, MD (US)

(73) Assignee: Terumo Kabushiki Kaisha, Tokyo (JP)

( * ) Notice: Subject to any disclaimer, the term of this patent is extended or adjusted under 35 U.S.C. 154(b) by 1122 days.

(21) Appl. No.: 16/933,230

(22) Filed: Jul. 20, 2020

(65) Prior Publication Data

US 2020/0345919 A1   Nov. 5, 2020

Related U.S. Application Data

(63) Continuation of application No. PCT/JP2018/003720, filed on Feb. 5, 2018, and a
(Continued)

(51) Int. Cl.
*B01D 63/02* (2006.01)
*A61M 1/16* (2006.01)
(Continued)

(52) U.S. Cl.
CPC ........... *B01D 63/02* (2013.01); *A61M 1/1625* (2014.02); *A61M 1/1629* (2014.02);
(Continued)

(58) Field of Classification Search
CPC .............. A61M 1/1698; A61M 1/1625; A61M 1/1629; A61M 1/3623; A61M 2207/10; B01D 65/003; B01D 69/08
See application file for complete search history.

(56) References Cited

U.S. PATENT DOCUMENTS

| 5,578,267 A | 11/1996 | Cosentino et al. |
| 8,747,742 B2 | 6/2014 | Kawamura et al. |

(Continued)

FOREIGN PATENT DOCUMENTS

| CN | 105899245 A | * | 8/2016 | .......... A61M 1/1629 |
| CN | 107638601 A | | 1/2018 | |

(Continued)

OTHER PUBLICATIONS

International Search Report, PCT/JP2019/003958, Apr. 16, 2019.
(Continued)

*Primary Examiner* — Susan S Su
*Assistant Examiner* — Eric Rassavong
(74) *Attorney, Agent, or Firm* — MacMillan, Sobanski & Todd, LLC

(57) ABSTRACT

In manufacturing an oxygenator (10), an intermediate spacer (18) is arranged between an inner cylinder unit (13) configured by winding a first hollow fiber membrane (14a) and an outer cylinder unit (15) configured by winding a second hollow fiber membrane (16a) so that a first gap (100a) is formed between one end portions of the inner cylinder unit (13) and the outer cylinder unit (15), and a first partition section (62a) is inserted into the first gap (100a). A first end portion (18a) of the intermediate spacer (18) is located at a region which does not overlap the first partition section (62a) in a radial direction. The intermediate spacer (18) independently supports the outer cylinder unit (15) in a state in which a gap (Sa) is formed between an inner peripheral surface of the intermediate spacer (18) and an outer peripheral surface of the inner cylinder unit (13).

14 Claims, 16 Drawing Sheets

Related U.S. Application Data continuation of application No. PCT/JP2019/003958, filed on Feb. 5, 2019.

(51) Int. Cl.
*A61M 1/36* (2006.01)
*B01D 65/00* (2006.01)
*B01D 69/08* (2006.01)

(52) U.S. Cl.
CPC ........ *A61M 1/1698* (2013.01); *A61M 1/3623* (2022.05); *B01D 65/003* (2013.01); *B01D 69/08* (2013.01); *A61M 2207/10* (2013.01); *B01D 2313/20* (2013.01)

(56) References Cited

U.S. PATENT DOCUMENTS

| | | | |
|---|---|---|---|
| 8,864,700 | B2 | 10/2014 | Kawamura et al. |
| 8,865,067 | B2 * | 10/2014 | Olson ................. B01D 63/025 422/45 |
| 10,098,994 | B2 | 10/2018 | Silvestri et al. |
| 10,807,043 | B2 * | 10/2020 | Mizoguchi .......... A61M 1/1623 |
| 2002/0039543 | A1 | 4/2002 | Ikeda et al. |
| 2018/0207344 | A1 | 7/2018 | Hisamatsu et al. |

FOREIGN PATENT DOCUMENTS

| | | | | |
|---|---|---|---|---|
| EP | 1839691 A1 | 3/2007 | | |
| JP | 2015136383 A | 7/2015 | | |
| WO | WO-2016009780 A1 * | 1/2016 | ............ | A61M 1/14 |
| WO | WO-2018062271 A1 * | 4/2018 | .......... | A61M 1/1629 |

OTHER PUBLICATIONS

Extended European Search Report, EP19748445.4, Mar. 9, 2021.
CN Office Action 102980007181.1, Jan. 9, 2023.
Translation of Written Opinion of the ISA, PCT/JP2019/003958, Apr. 16, 2019.

* cited by examiner

OXYGENATOR AND METHOD FOR MANUFACTURING THE SAME

CROSS REFERENCE TO RELATED APPLICATIONS

This application is a continuation of PCT Application No. PCT/JP2018/003720, filed Feb. 5, 2018, and a continuation of PCT Application No. PCT/JP2019/003958, filed Feb. 5, 2019, both of which are incorporated herein by reference in their entirety.

BACKGROUND OF THE INVENTION

The present invention relates to an oxygenator in which a cylindrical heat exchange unit produced by winding a first hollow fiber membrane and a cylindrical gas exchange unit produced by winding a second hollow fiber membrane are accommodated in a housing in a state of being disposed to overlap each other in a radial direction so that a blood flow path is formed on an outer side of the first hollow fiber membrane and an outer side of the second hollow fiber membrane, and a method for manufacturing the same.

This kind of oxygenator is disclosed in, for example, WO2016/009780A. The housing of this oxygenator includes a pair of cylindrical partition sections which partitions spaces on both sides extending in the axial direction from the heat exchange unit and the gas exchange unit into a heat medium flow path and a gas flow path.

In the oxygenator described above, a partition section is inserted between the end portions of the heat exchange unit (inner cylinder unit) and the gas exchange unit (outer cylinder unit) when the housing is assembled in some cases. However, in the conventional oxygenator, the second hollow fiber membrane of the gas exchange unit is wound around the outer surface of the first hollow fiber membrane of the heat exchange unit, and thus the end portion of the heat exchange unit and the end portion of the gas exchange unit are pushed in the radial direction by the partition section during assembly. In this case, there is the possibility that the lumen of the first hollow fiber membrane and the lumen of the second hollow fiber membrane are collapsed and the heat exchange rate and the gas exchange rate decrease.

The present invention has been made in view of such problems, and an object thereof is to provide an oxygenator capable of alleviating decreases in a heat exchange rate and a gas exchange rate even in a case in which each of the heat exchange unit and the gas exchange unit is formed by winding a hollow fiber membrane, and a method for manufacturing the same.

SUMMARY OF THE INVENTION

In order to achieve the above object, the oxygenator according to the present invention is an oxygenator in which an inner cylinder unit configured as one of a heat exchange unit or a gas exchange unit is produced by winding a first hollow fiber membrane and an outer cylinder unit configured as the other of the heat exchange unit or the gas exchange unit is produced by winding a second hollow fiber membrane. The inner and outer cylinder units are accommodated in a housing in a state of being disposed to overlap each other in a radial direction so that a blood flow path is formed on an outer side of the first hollow fiber membrane and an outer side of the second hollow fiber membrane. The housing includes a pair of partition sections that partitions each of spaces on both sides in an axial direction from the inner cylinder unit and the outer cylinder unit into a heat medium flow path and a gas flow path. Protruding ends of the partition sections are each inserted between end portions of the inner cylinder unit and the outer cylinder unit. A cylindrical intermediate spacer is arranged between the inner cylinder unit and the outer cylinder unit, at least one end portion of the intermediate spacer is located in a region that does not overlap the partition section in a radial direction in end portions of the inner cylinder unit and the outer cylinder unit, and the intermediate spacer is configured to be able to independently support the outer cylinder unit in a state in which a gap is formed between an inner peripheral surface of the intermediate spacer and an outer peripheral surface of the inner cylinder unit.

According to such a configuration, it is possible to form a gap, into which the protruding end of a partition section can be inserted, between the end portions of the inner cylinder unit and the outer cylinder unit by the intermediate spacer. Hence, the end portion of the inner cylinder unit and the end portion of the outer cylinder unit are engaged in the radial direction by the partition section (instead of abutting axially) and it is possible to prevent the lumen of the first hollow fiber membrane and the lumen of the second hollow fiber membrane from being collapsed. Consequently, it is possible to avoid decreases in the heat exchange rate and the gas exchange rate. In addition, the intermediate spacer is configured to be able to independently support the outer cylinder unit in a state in which a gap is formed between the inner peripheral surface of the intermediate spacer and the outer peripheral surface of the inner cylinder unit, and thus the tightening force of the second hollow fiber membrane can be effectively received by the intermediate spacer. Hence, it is possible to prevent the lumen of the first hollow fiber membrane from being collapsed by the tightening force of the second hollow fiber membrane.

In the oxygenator, a radial thickness of a protruding end part of the partition section inserted between end portions of the inner cylinder unit and the outer cylinder unit may be thinner than a radial wall thickness of the intermediate spacer.

According to such a configuration, it is possible to further prevent the lumen of the first hollow fiber membrane and the lumen of the second hollow fiber membrane from being collapsed by the partition section.

In some embodiments of the oxygenator, the intermediate spacer may have a plurality of annular portions that are arrayed in the axial direction and each extending in a circumferential direction, a connection portion that connects the annular portions adjacent to each other in the axial direction to each other, and a slit between the annular portions adjacent to each other to form a blood flow path.

According to such a configuration, it is possible to effectively improve the rigidity of the intermediate spacer in the radial direction. Hence, the tightening force of the second hollow fiber membrane can be reliably accommodated by the intermediate spacer.

In some embodiments of the oxygenator, a plurality of connection portions may be provided in the circumferential direction of the intermediate spacer.

According to such a configuration, it is possible to more effectively improve the rigidity of the intermediate spacer in the radial direction.

In some embodiments of the oxygenator, the annular portions may be each formed so that a thickness along the axial direction decreases radially outward.

According to such a configuration, it is possible to decrease the contact area between the second hollow fiber membrane and the intermediate spacer and thus to efficiently bring blood into contact with the second hollow fiber membrane.

In some embodiments of the oxygenator, a protrusion that suppresses movement of the intermediate spacer in the axial direction with respect to the inner cylinder unit by coming into contact with the inner cylinder unit and forms a gap between an inner peripheral surface of the intermediate spacer and an outer peripheral surface of the inner cylinder unit may be provided on an inner surface of the intermediate spacer.

According to such a configuration, it is possible not only to suppress the displacement of the intermediate spacer in the axial direction with respect to the inner cylinder unit and the outer cylinder unit by the protrusion but also to effectively prevent collapse of the lumen of the first hollow fiber membrane by preventing the transmission of the tightening force of the second hollow fiber membrane to the first hollow fiber membrane.

In the oxygenator, a protruding length of the protrusion may be equal to or less than an outer diameter of the first hollow fiber membrane.

According to such a configuration, it is possible to locate the protrusion between the first hollow fiber membranes adjacent to each other. In this manner, it is possible to effectively prevent the displacement of the intermediate spacer in the axial direction with respect to the inner cylinder unit.

In some embodiments of the oxygenator, the protrusion may be formed so that a dimension along an axial direction decreases radially inward.

According to such a configuration, it is possible to efficiently locate the tip portion of the protrusion between the first hollow fiber membranes adjacent to each other.

In some embodiments of the oxygenator, the protrusion may be located at a site of an inner surface of each of the annular portions, the site being adjacent to the connection portion.

According to such a configuration, it is possible to dispose the protrusion at the part having a relatively large area of the inner surface of the intermediate spacer and thus to improve the rigidity of the protrusion.

In some embodiments of the oxygenator, each end portion of the intermediate spacer may be located at a region that does not overlap the partition section in a radial direction in end portions of the inner cylinder unit and the outer cylinder unit.

According to such a configuration, it is possible to form a gap, into which the partition section can be inserted, between the end portions of both the inner cylinder unit and the outer cylinder unit by the intermediate spacer. Consequently, it is possible to further prevent decreases in the heat exchange rate and the gas exchange rate.

One method for manufacturing an oxygenator according to the present invention is a method for manufacturing an oxygenator including an inner cylinder unit configured as one of a heat exchange unit or a gas exchange unit and an outer cylinder unit configured as the other of the heat exchange unit or the gas exchange unit that are disposed to overlap each other in a radial direction, the method sequentially performing: a first winding step of forming a first cylindrical unit by winding a first hollow fiber membrane on an outer surface of a core; an arrangement step of arranging a cylindrical intermediate spacer on an outer surface of the first cylindrical unit; a second winding step of forming a second cylindrical unit by winding a second hollow fiber membrane around an outer surface of the intermediate spacer; an outer cylinder disposition step of disposing an outer cylinder so as to cover an outer surface of the second cylindrical unit; a cutting step of forming the inner cylinder unit and the outer cylinder unit by cutting both end portions of the first cylindrical unit and the second cylindrical unit; a sealing step of sealing outer sides of the first hollow fiber membrane and the second hollow fiber membrane at both end portions of the inner cylinder unit and the outer cylinder unit with a sealing member; and a mounting step of mounting cover members on both end portions of the core and the outer cylinder and forming a heat medium flow path and a gas flow path in the respective cover members, in which the intermediate spacer is configured to be able to independently support the outer cylinder unit in a state in which a gap is formed between an inner peripheral surface of the intermediate spacer and an outer peripheral surface of the inner cylinder unit, the intermediate spacer is arranged on an outer surface of the first cylindrical unit so that a gap is formed at least between one end portions of the inner cylinder unit and the outer cylinder unit or between the other end portions of the inner cylinder unit and the outer cylinder unit when performing the mounting step in the arrangement step, and a partition section of the cover member is inserted into the gap formed by the intermediate spacer in the mounting step.

According to such a method, it is possible to manufacture the oxygenator described above.

In the method for manufacturing an oxygenator, an annular member may be disposed so as to cover only both end portions of the first cylindrical unit in the arrangement step, the second hollow fiber membrane may be wound around an outer surface of each of the intermediate spacer and the annular member in the second winding step, and a removal step of removing the annular member may be performed after the sealing step.

According to such a method, it is possible to reliably form a gap, into which the partition section can be inserted, between the end portions of both the inner cylinder unit and the outer cylinder unit by the annular member.

In some embodiments of the method for manufacturing an oxygenator, the intermediate spacer may be arranged by disposing a plurality of divided spacers divided in a circumferential direction on an outer surface of the first cylindrical unit and connecting the divided spacers to each other in the arrangement step.

According to such a method, it is possible to easily arrange the cylindrical intermediate spacer on the outer surface of the first cylindrical unit.

In some embodiments of the method for manufacturing an oxygenator, the intermediate spacer may be arranged on an outer surface of the first cylindrical unit so that the gap is formed between one end portions of the inner cylinder unit and the outer cylinder unit and between the other end portions of the inner cylinder unit and the outer cylinder unit when performing the mounting step in the arrangement step and the partition section of each of the cover members may be inserted into each of the gaps formed by the intermediate spacer in the mounting step.

According to such a method, it is possible to further prevent decreases in the heat exchange rate and the gas exchange rate.

In some embodiments of the method for manufacturing an oxygenator, the first cylindrical unit may be formed by circumferentially winding one continuous first hollow fiber membrane around the outer surface of the first cylindrical unit and reciprocating the one continuous first hollow fiber membrane a plurality of times in an axial direction in the first winding step and the second cylindrical unit may be formed by circumferentially winding one continuous second hollow fiber membrane around the outer surface of the intermediate spacer and reciprocating the one continuous second hollow fiber membrane a plurality of times in the axial direction in the second winding step.

According to such a method, it is possible to efficiently form the first cylindrical unit and the second cylindrical unit.

According to the present invention, it is possible to form a gap, into which a partition section can be inserted, between end portions of a heat exchange unit and a gas exchange unit by an intermediate spacer and thus to prevent a lumen of a first hollow fiber membrane and a lumen of a second hollow fiber membrane from being collapsed by the partition section. Consequently, it is possible to prevent decreases in the heat exchange rate and the gas exchange rate.

DETAILED DESCRIPTION OF PREFERRED EMBODIMENTS

Hereinafter, suitable embodiments of the oxygenator according to the present invention will be described with reference to the attached drawings in relation to a method for manufacturing the same.

Figure 1:
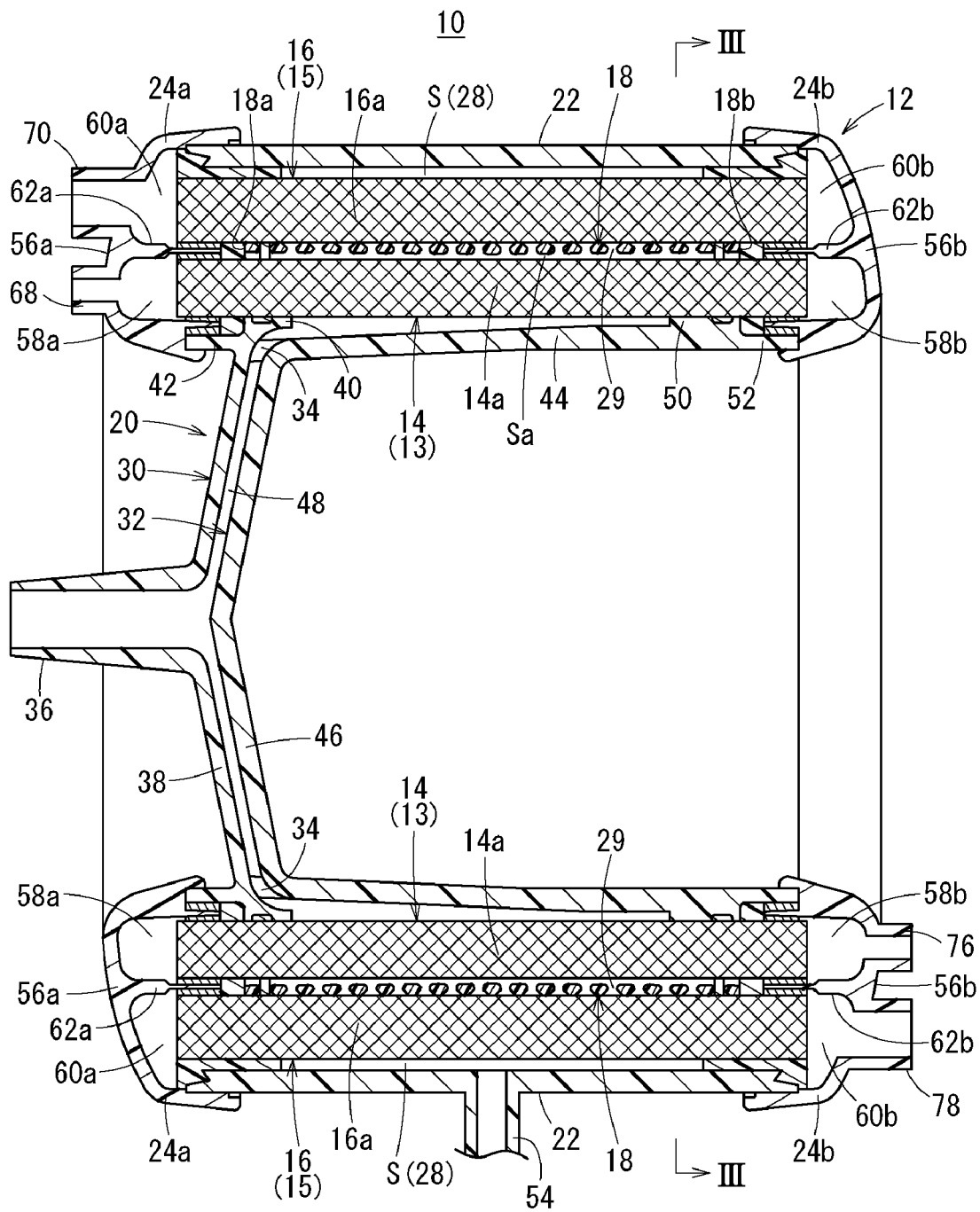
FIG. 1 is a longitudinal sectional view of an oxygenator according to an embodiment of the present invention.

As illustrated in FIG. 1, an oxygenator 10 according to an embodiment of the present invention is a medical instrument that temporarily substitutes for the function of lung in the operation of heart surgery and the like of a human body. Specifically, the oxygenator 10 is a device for adjusting the blood temperature, removing carbon dioxide in blood, and supplying oxygen to blood in extracorporeal blood circulation.

Figure 2:
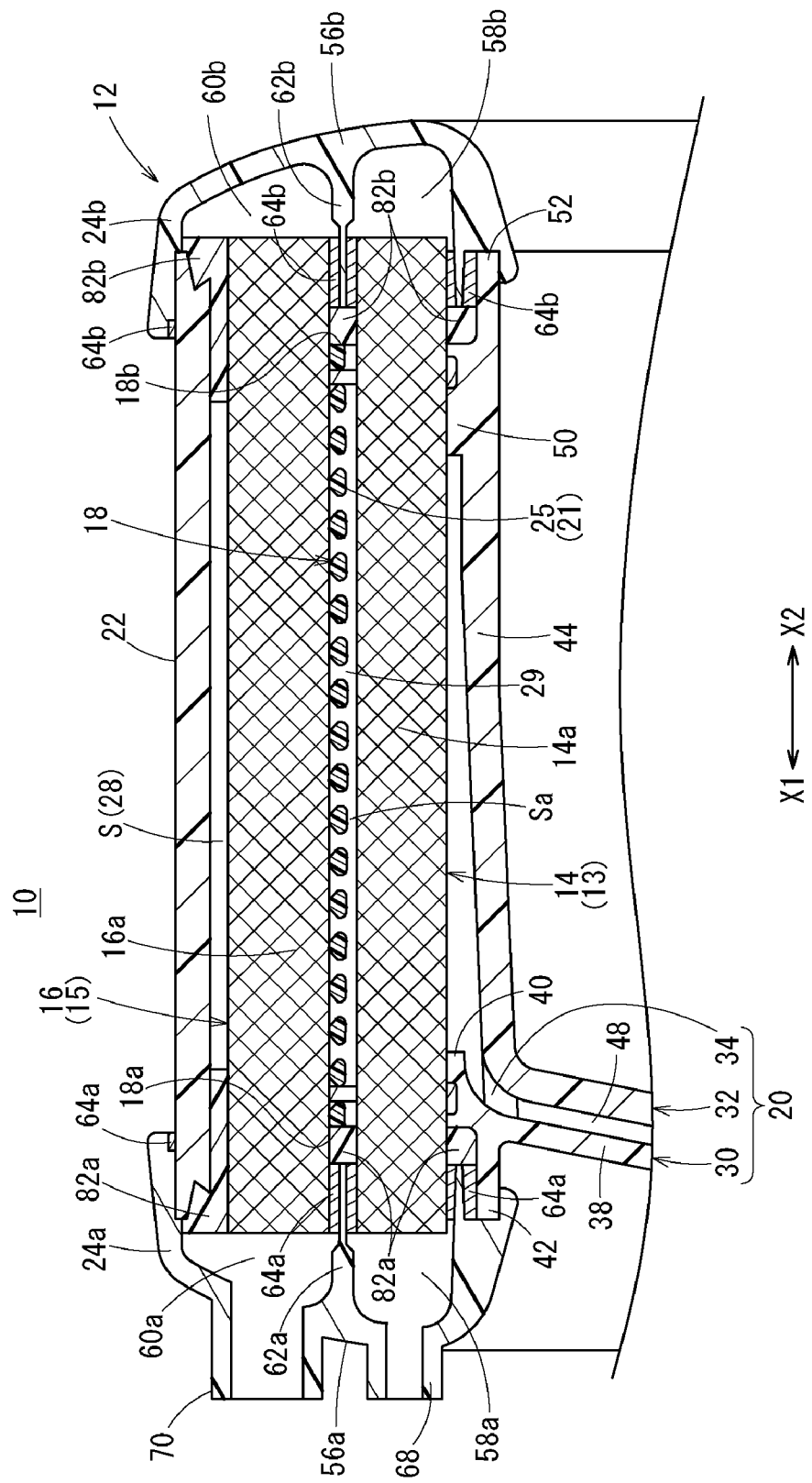
FIG. 2 is a partially enlarged sectional view of the oxygenator illustrated in FIG. 1.
Figure 3:
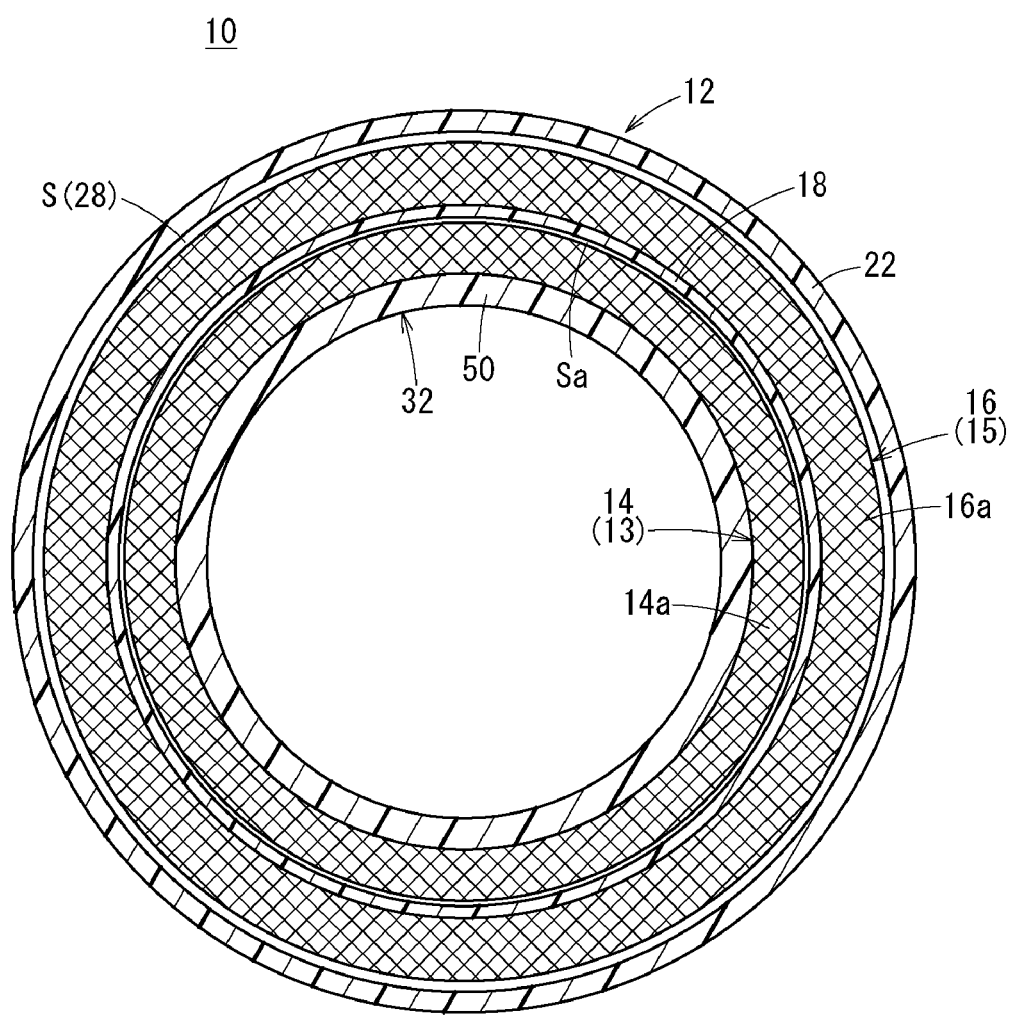
FIG. 3 is a transverse sectional view taken along the line III-III in FIG. 1.

As illustrated in FIGS. 1 to 3, the oxygenator 10 includes a housing 12, a heat exchange unit 14 which is an inner cylinder unit 13, a gas exchange unit 16 which is an outer cylinder unit 15, and an intermediate spacer 18.

In FIG. 1, the housing 12 includes a core 20 constituting a central part of the oxygenator 10, an outer cylinder 22 provided on an outer peripheral side of the core 20, a first cover member 24a mounted on one end portion of the core 20 and one end portion of the outer cylinder 22, and a second cover member 24b mounted on the other end portion of the core 20 and the other end portion of the outer cylinder 22.

The core 20, the outer cylinder 22, the first cover member 24a, and the second cover member 24b form an annular accommodation space S for accommodating the cylindrical heat exchange unit 14 and the cylindrical gas exchange unit 16. The accommodation space S functions as a blood flow path 28. Each of the core 20, the outer cylinder 22, the first cover member 24a, and the second cover member 24b is integrally formed of a hard resin.

The core 20 includes a first core section 30 constituting one end portion of the core 20 and a second core section 32 constituting a part including the other end portion of the core 20. The first core section 30 and the second core section 32 are connected to each other by a plurality of connection portions 34.

The first core section 30 has a blood inflow portion 36 to which a tube (not illustrated) can be connected at one end portion and an annular wall portion 38 extending radially outward from the blood inflow portion 36. The outer end portion of the wall portion 38 is provided with a first support portion 40 for supporting the heat exchange unit 14 and a first annular convex portion 42 protruding from the first support portion 40 to one side (the arrow X1 direction in FIG. 1) of the outer cylinder 22 in the axial direction.

The second core section 32 is formed in a bottomed cylindrical shape and has a cylinder portion 44 and a closing portion 46 provided at one end portion (the end portion in the arrow X1 direction) of the cylinder portion 44. The closing portion 46 is disposed so as to face the wall portion 38 with a gap. The gap between the closing portion 46 and the wall portion 38 functions as a blood introduction path 48 for guiding the blood flowing from the blood inflow portion 36 into the accommodation space S. The outer surface of the cylinder portion 44 is provided with a second support portion 50 for supporting the heat exchange unit 14 and a second annular convex portion 52 protruding from the second support portion 50 to the other end side (the arrow X2 direction in FIG. 1) of the outer cylinder 22 in the axial direction. The second support portion 50 is located at the other end portion of the cylinder portion 44.

The outer cylinder 22 is a cylindrical member disposed radially outward from the core 20 with a gap (see FIG. 3). The entire length of the outer cylinder 22 in the axial direction is slightly longer than the entire length of the second core section 32 in the axial direction. The outer cylinder 22 is provided with a blood outflow portion 54 for allowing blood in the accommodation space S to flow out.

As illustrated in FIGS. 1 and 2, the first cover member 24a has a first cover main body 56a provided so as to face one end surface of the heat exchange unit 14 and one end surface of the gas exchange unit 16 with a gap and a first partition section 62a which partitions a space in the first cover main body 56a into a first heat medium flow path 58a and a first gas flow path 60a.

The first cover main body 56a extends in an annular shape and in the axial direction. The inner end portion (radially inner end portion) of the first cover main body 56a is fixed to the first annular convex portion 42 with an adhesive 64a. The outer end portion (radially outer end portion) of the first cover main body 56a is fixed to the outer cylinder 22 with the adhesive 64a. The first cover main body 56a is provided with a heat medium inflow portion 68 for allowing a heat medium to flow into the first heat medium flow path 58a and a gas inflow portion 70 for allowing a gas (oxygen gas) to flow into the first gas flow path 60a.

The first partition section 62a protrudes in the axial direction from the inner surface of the first cover main body 56a toward the side on which the heat exchange unit 14 and the gas exchange unit 16 are located and extends annularly. The protruding end portion of the first partition section 62a is fixed with the adhesive 64a in the state of being inserted between one end portions of the heat exchange unit 14 and the gas exchange unit 16. The thickness (in the radial direction) of the protruding end portion of the first partition section 62a (the part inserted between one end portions of the heat exchange unit 14 and the gas exchange unit 16 of the first partition section 62a) is thinner than the wall thickness of the intermediate spacer 18. The thickness of the root portion of the first partition section 62a (the part near the first cover main body 56a) is thicker than the thickness of the protruding end portion of the first partition section 62a.

The first heat medium flow path 58a is a flow path for guiding the heat medium to the heat exchange unit 14 and is located radially inward from the first partition section 62a. The first gas flow path 60a is a path for guiding the oxygen gas to the gas exchange unit 16 and is located radially outward from the first partition section 62a.

The second cover member 24b has a second cover main body 56b provided so as to face the other end surface of the heat exchange unit 14 and the other end surface of the gas exchange unit 16 with a gap and a second partition section 62b which partitions a space in the second cover main body 56b into a second heat medium flow path 58b and a second gas flow path 60b.

The second cover main body 56b extends annularly. The inner end portion of the second cover main body 56b is fixed to the second annular convex portion 52 with an adhesive 64b. The outer end portion of the second cover main body 56b is fixed to the outer cylinder 22 with the adhesive 64b. In FIG. 1, the second cover main body 56b is provided with a heat medium outflow portion 76 for allowing the heat medium in the second heat medium flow path 58b to flow out and a gas outflow portion 78 for allowing the gas (carbon dioxide gas) in the second gas flow path 60b to flow out to the outside.

As illustrated in FIGS. 1 and 2, the second partition section 62b protrudes from the inner surface of the second cover main body 56b toward the side on which the heat exchange unit 14 and the gas exchange unit 16 are located and extends in an annular shape. The protruding end portion of the second partition section 62b is liquid-tightly and air-tightly fixed with the adhesive 64b in the state of being inserted between the other end portions of the heat exchange unit 14 and the gas exchange unit 16. The radial thickness of the protruding end portion of the second partition section 62b (the part inserted between the other end portions of the heat exchange unit 14 and the gas exchange unit 16 of the second partition section 62b) is thinner than the wall thickness of the intermediate spacer 18. The thickness of the root portion of the second partition section 62b (the part near the second cover main body 56b) is thicker than the thickness of the protruding end portion of the second partition section 62b.

The second heat medium flow path 58b is a flow path for guiding the heat medium guided from the heat exchange unit 14 to the heat medium outflow portion 76 and is located radially inward from the second partition section 62b. The second gas flow path 60b is a flow path for guiding the gas (carbon dioxide gas) guided from the gas exchange unit 16 to the gas outflow portion 78 and is located radially outward from the second partition section 62b.

The heat exchange unit 14 is for performing heat exchange between the blood flowing in the blood flow path 28 and the heat medium. As the heat medium, for example, water (pure water) is used. However, the heat medium is not limited to water and may be another liquid or a gas. The entire length of the heat exchange unit 14 is slightly longer than the entire length of the outer cylinder 22. In other words, both end portions of the heat exchange unit 14 protrude to the outer side of the outer cylinder 22.

The heat exchange unit 14 is formed in a cylindrical shape by a plurality of first hollow fiber membranes 14a. Each first hollow fiber membrane 14a is wound around the outer surface of the core 20 (the first support portion 40 and the second support portion 50) so as to extend over the entire length of the heat exchange unit 14. A gap through which blood can flow is formed between the first hollow fiber membranes 14a adjacent to each other. The opening at one end of each first hollow fiber membrane 14a communicates with the interior of the first heat medium flow path 58a, and the opening at the other end of each first hollow fiber membrane 14a communicates with the interior of the second heat medium flow path 58b. In other words, the heat medium flows through the lumen of each first hollow fiber membrane 14a.

The first hollow fiber membrane 14a is configured so as not to allow the heat medium and blood to pass therethrough. As a constituent material for the first hollow fiber membrane 14a, for example, polymer materials such as polypropylene, polyamide, polyethylene, polysulfone, polyacrylonitrile, polytetrafluoroethylene, and polymethylpentene are used and polyamide is preferable. The inner diameter of the first hollow fiber membrane 14a is preferably set to, for example, a range of 50 μm to 700 μm. In this case, the flow resistance of the heat medium flowing through the lumen of the first hollow fiber membrane 14a can be decreased to a relatively low value. The outer diameter of the first hollow fiber membrane 14a is preferably set to a range of 100 μm to 1000 μm, and more preferably to a range of 120 μm to 800 μm. In this case, the surface area of the first hollow fiber membrane 14a can be efficiently increased.

The gas exchange unit 16 is for supplying oxygen gas to the blood flowing through the blood flow path 28 and removing carbon dioxide in the blood. The gas exchange unit 16 is provided on the outer peripheral side of the heat exchange unit 14. In other words, the gas exchange unit 16 and the heat exchange unit 14 are disposed so as to overlap each other in the radial direction. The entire length of the gas exchange unit 16 is the same as the entire length of the heat exchange unit 14.

The gas exchange unit 16 is formed in a cylindrical shape by a plurality of second hollow fiber membranes 16a. Each second hollow fiber membrane 16a is wound around the outer surface of the intermediate spacer 18 arranged on the outer surface of the heat exchange unit 14 so as to extend over the entire length of the gas exchange unit 16. A gap through which blood can flow is formed between the second hollow fiber membranes 16a adjacent to each other. Then opening at one end of each second hollow fiber membrane 16a communicates with the interior of the first gas flow path 60a, and the opening at the other end of each second hollow fiber membrane 16a communicates with the interior of the second gas flow path 60b. In other words, gas (oxygen gas and carbon dioxide gas) flows through the lumen of each second hollow fiber membrane 16a.

The second hollow fiber membrane 16a is configured so as to allow oxygen gas and carbon dioxide gas to pass therethrough while not allowing blood to pass therethrough. The constituent material for and inner diameter of the second hollow fiber membrane 16a can be set in the same manner as the constituent material for and inner diameter of the first hollow fiber membrane 14a.

As illustrated in FIGS. 1 to 3, the intermediate spacer 18 is arranged on the outer peripheral surface of the heat exchange unit 14. In other words, the intermediate spacer 18 is provided between the heat exchange unit 14 and the gas exchange unit 16. The intermediate spacer 18 is formed in a cylindrical shape and has a first end portion 18a and a second end portion 18b.

In FIGS. 1 and 2, the first end portion 18a (the end portion in the arrow X1 direction) of the intermediate spacer 18 is located at the part which does not overlap the first partition section 62a in the radial direction in one end portions of the heat exchange unit 14 and the gas exchange unit 16. In other words, the first end portion 18a of the intermediate spacer 18 is located near the protruding end of the first partition section 62a. In other words, the first end portion 18a of the intermediate spacer 18 is located by being slightly shifted (in the axial direction) on the second cover member 24b side (arrow X2 direction) from the protruding end of the first partition section 62a.

The second end portion 18b (the end portion in the arrow X2 direction) of the intermediate spacer 18 is located at the part which does not overlap the second partition section 62b in the radial direction in the other end portions of the heat exchange unit 14 and the gas exchange unit 16. In other words, the second end portion 18b of the intermediate spacer 18 is located near the protruding end of the second partition section 62b. In other words, the second end portion 18b of the intermediate spacer 18 is located by being slightly shifted (in the axial direction) on the first cover member 24a side (arrow X1 direction) from the protruding end of the second partition section 62b.

Figure 4:
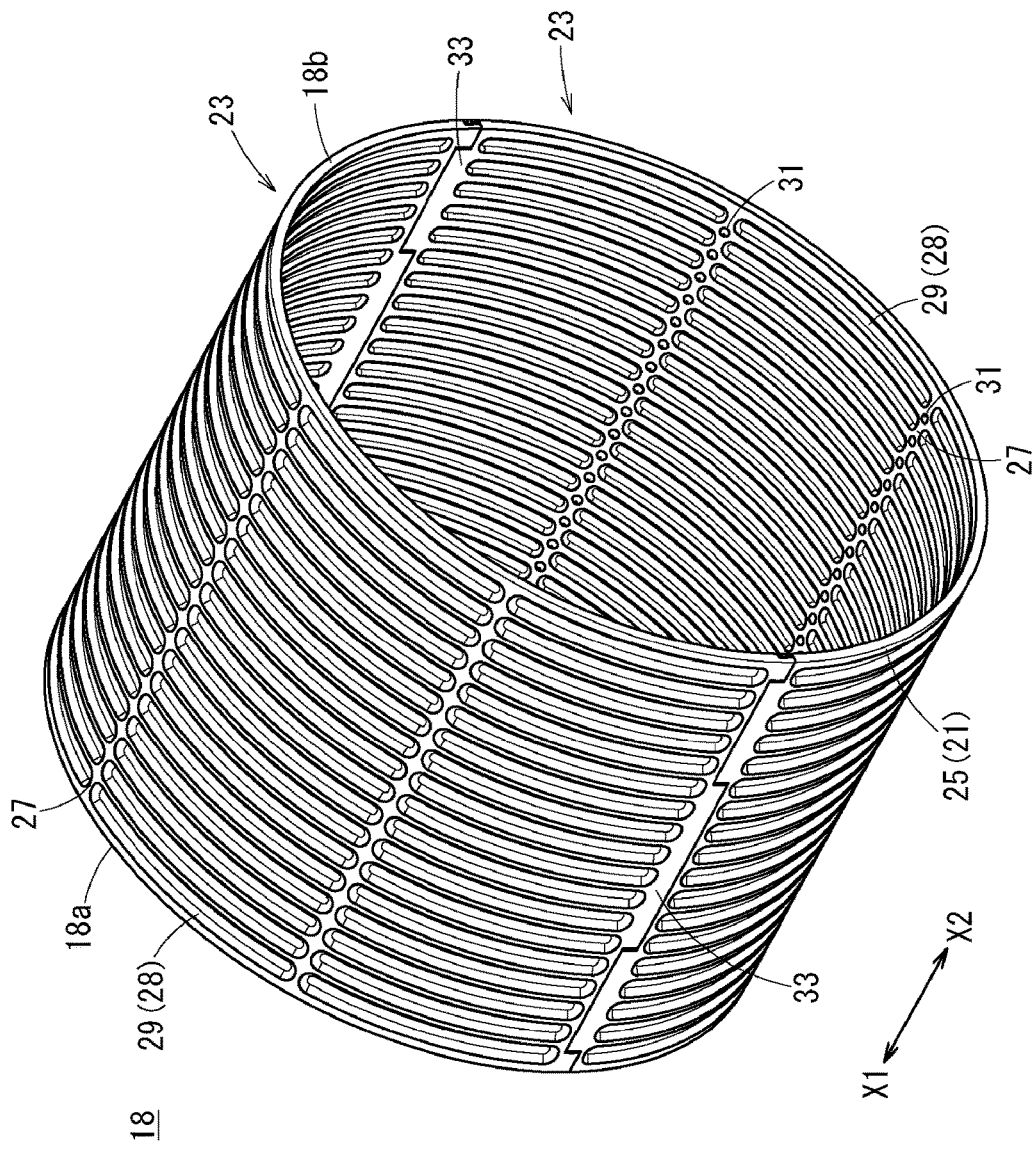
FIG. 4 is a perspective view of an intermediate spacer.
Figure 5:
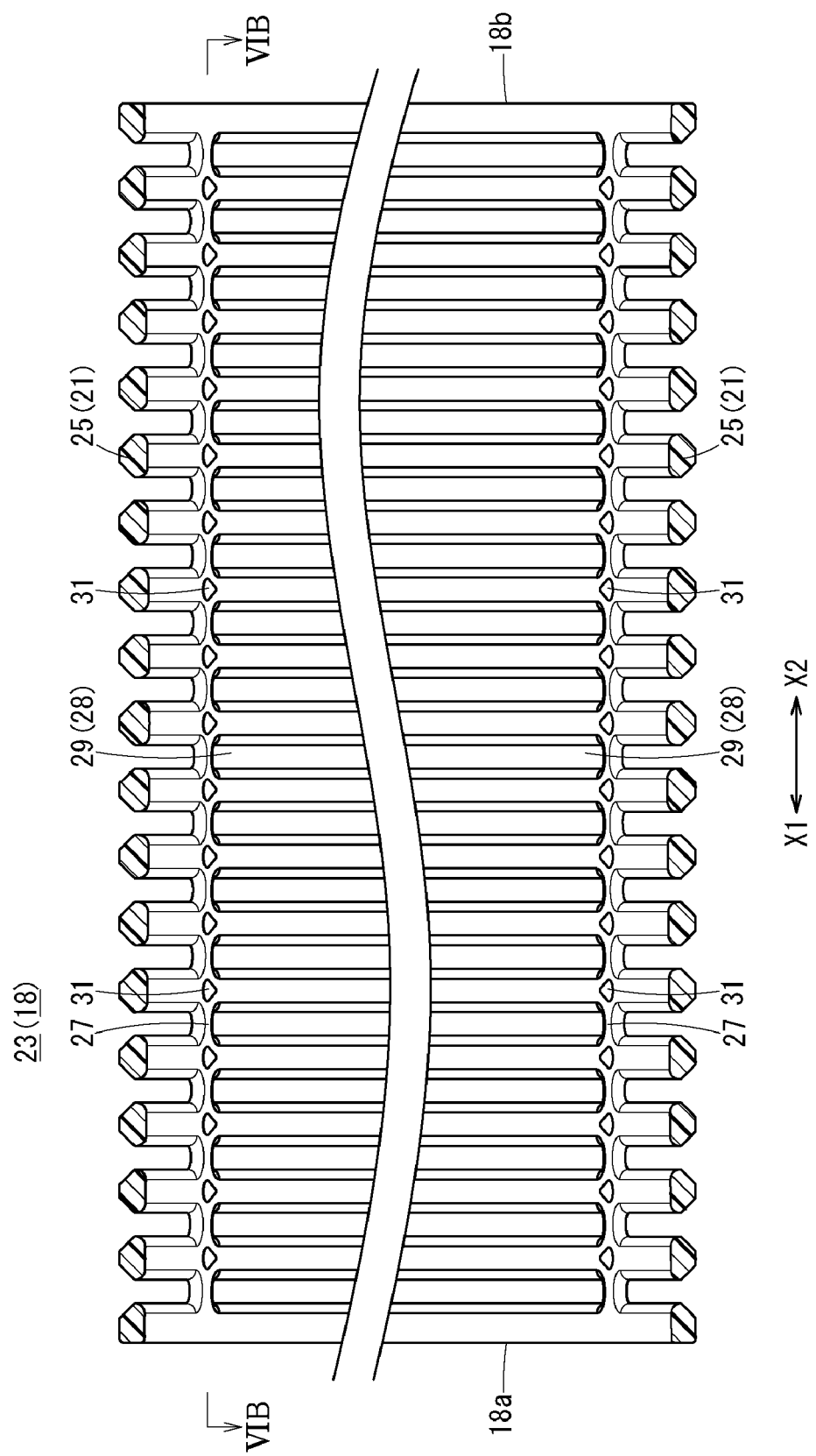
FIG. 5 is a partially omitted longitudinal sectional view of an intermediate spacer.

As illustrated in FIGS. 4 and 5, the intermediate spacer 18 is configured to be able to independently support the gas exchange unit 16 in a state in which a gap Sa (see FIGS. 2 and 3) is formed between the inner peripheral surface of the intermediate spacer 18 and the outer peripheral surface of the inner cylinder unit 13 (heat exchange unit 14). In other words, the gap Sa is entirely or partially formed between the inner peripheral surface of the intermediate spacer 18 and the outer peripheral surface of the inner cylinder unit 13. The gap Sa may be formed in a state in which the entire inner peripheral surface of the intermediate spacer 18 and the entire outer peripheral surface of the inner cylinder unit 13 are separated from each other or may be formed in a state in which a part of the inner peripheral surface of the intermediate spacer 18 is in contact with a part of the outer peripheral surface of the inner cylinder unit 13. The rigidity of the intermediate spacer 18 is greater than the rigidity of the first hollow fiber membrane 14a and the second hollow fiber membrane 16a. The intermediate spacer 18 is cylindrical and has a plurality of annular portions 21 which are arranged in the axial direction and extend in the circumferential direction. The plurality of annular portions 21 is provided to be parallel to each other in the circumferential direction and regularly spaced in the axial direction.

The intermediate spacer 18 is formed in a cylindrical shape by connecting two semi-cylindrical spacers 23 divided in the circumferential direction to each other. The respective divided spacers 23 are integrally injection-molded with a hard resin. The two divided spacers 23 have the same configuration as each other.

The divided spacer 23 has a plurality of peripheral wall portions 25 extending in the circumferential direction of the intermediate spacer 18 and a plurality of connection portions 27 connecting adjacent peripheral wall portions 25 to each other. The peripheral wall portion 25 forms a part of the annular portion 21.

Each peripheral wall portion 25 extends in a semicircular shape. The plurality of peripheral wall portions 25 is disposed by being separated at regular intervals along the axial direction (the arrow X1 direction and the arrow X2 direction) of the intermediate spacer 18. In other words, a slit 29 as a blood flow path 28 through which blood flows is formed between the peripheral wall portions 25 adjacent to each other in the axial direction of the intermediate spacer 18. The slit 29 is formed between the connection portions 27 adjacent to each other in the circumferential direction of the intermediate spacer 18. The slit 29 extends in the circumferential direction of the intermediate spacer 18. Each peripheral wall portion 25 is formed so that the thickness along the axial direction decreases at the radially outward surface of the intermediate spacer 18.

Figure 6A:
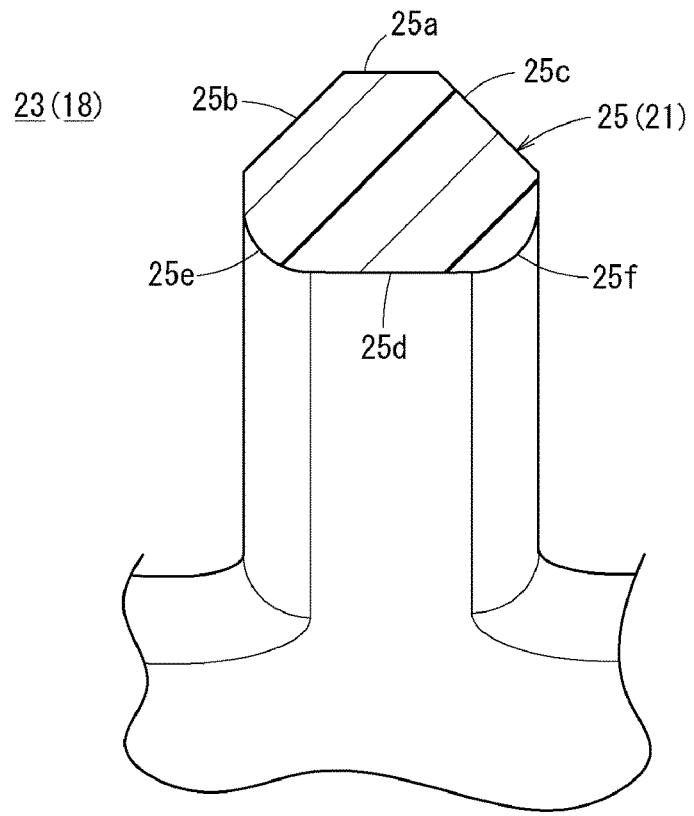
FIG. 6A is a partially enlarged view of FIG. 5

Specifically, as illustrated in FIG. 6A, the peripheral wall portion 25 located in the middle of the intermediate spacer 18 in the axial direction has an outer surface 25a, two inclined surfaces 25b and 25c, an inner surface 25d, and two curved surfaces 25e and 25f. The outer surface 25a is a most radially outward located surface of the peripheral wall portions 25 and extends along the axis of the intermediate spacer 18. The inclined surface 25b is inclined radially inward from the end of the outer surface 25a in the arrow X1 direction. The inclined surface 25c is inclined radially inward from the end of the outer surface 25a in the arrow X2 direction. The inner surface 25d is a most radially inward located surface of the peripheral wall portion 25 and extends along the axis of the intermediate spacer 18. The curved surface 25e extends in an arc shape and connects the inclined surface 25b and the inner surface 25d to each other. The curved surface 25f extends in an arc shape and connects the inclined surface 25c and the inner surface 25d to each other.

As illustrated in FIGS. 4 and 5, the peripheral wall portion 25 located at one end of the intermediate spacer 18 in the axial direction (the end in the arrow X1 direction) is provided with one end surface (first end portion 18a) extending in the direction orthogonal to the axis of the intermediate spacer 18 (i.e., radially flat) instead of the inclined surface 25b. The peripheral wall portion 25 located at the other end (the end in the arrow X2 direction) of the intermediate spacer 18 in the axial direction is provided with another radially-flat end surface (second end portion 18b) extending in the direction orthogonal to the axis of the intermediate spacer 18 instead of the inclined surface 25c. A plurality of (two in the example of FIG. 4) connection portions 27 of each semi-cylindrical divided spacer 23 is provided in the axial direction along the circumference of the cylindrical shape. The plurality of connection portions 27 is disposed in a straight line along the axial direction.

Figure 6B:
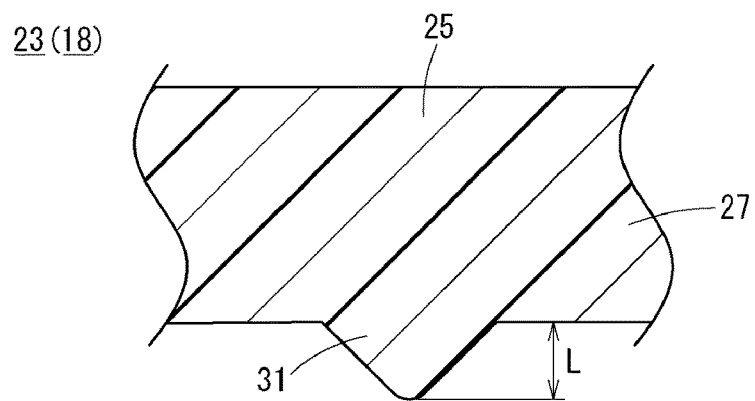
FIG. 6B is a partially omitted sectional view taken along the line VIB-VIB in FIG. 5.

A plurality of protrusions 31 which suppresses movement of the intermediate spacer 18 in the axial direction with respect to the inner cylinder unit 13 by coming into contact with the inner cylinder unit 13 and forms the gap Sa between the inner peripheral surface of the intermediate spacer 18 and the outer peripheral surface of the inner cylinder unit 13 (heat exchange unit 14) is provided on the inner surface of the divided spacer 23. The protrusions 31 are located at a site of the inner surface of the peripheral wall portion 25, the site adjacent to the connection portions 27. As illustrated in FIG. 6B, the protruding length L of each protrusion 31 is equal to or less than the outer diameter of the first hollow fiber membrane 14a. Each protrusion 31 is formed so that the dimension along the axial direction (the arrow X1 direction and the arrow X2 direction) decreases radially inward (i.e., each protrusion narrows from is base to its tip).

In FIG. 4, both end portions of the divided spacer 23 in the circumferential direction are provided with claw portions 33. The two divided spacers 23 form one intermediate spacer 18 as the claw portions 33 are joined to each other. The intermediate spacer 18 has a plurality of annular portions 21 formed by connecting the peripheral wall portions 25 of the respective divided spacers 23 to each other. The annular portions 21 extend in a substantially perfect circular shape.

As illustrated in FIG. 2, one end side of the accommodation space S is filled with a first sealing member 82a for preventing leakage of blood to the outside (the first heat medium flow path 58a and the first gas flow path 60a). Specifically, the first sealing member 82a is added between one end portion of the heat exchange unit 14 and the first annular convex portion 42, between one end portion of the heat exchange unit 14 and one end portion of the gas exchange unit 16, and between one end portion of the gas exchange unit 16 and one end portion of the outer cylinder 22.

The other end side of the accommodation space S is filled with a second sealing member 82b for preventing leakage of blood to the outside (the second heat medium flow path 58b and the second gas flow path 60b). Specifically, the second sealing member 82b is added between the other end portion of the heat exchange unit 14 and the second annular convex portion 52, between the other end portion of the heat exchange unit 14 and the other end portion of the gas exchange unit 16, and between the other end portion of the gas exchange unit 16 and the other end portion of the outer cylinder 22. For example, a resin such as urethane is used in each of the first sealing member 82a and the second sealing member 82b.

Next, the operation of the oxygenator 10 configured as described above will be described.

Figure 7:
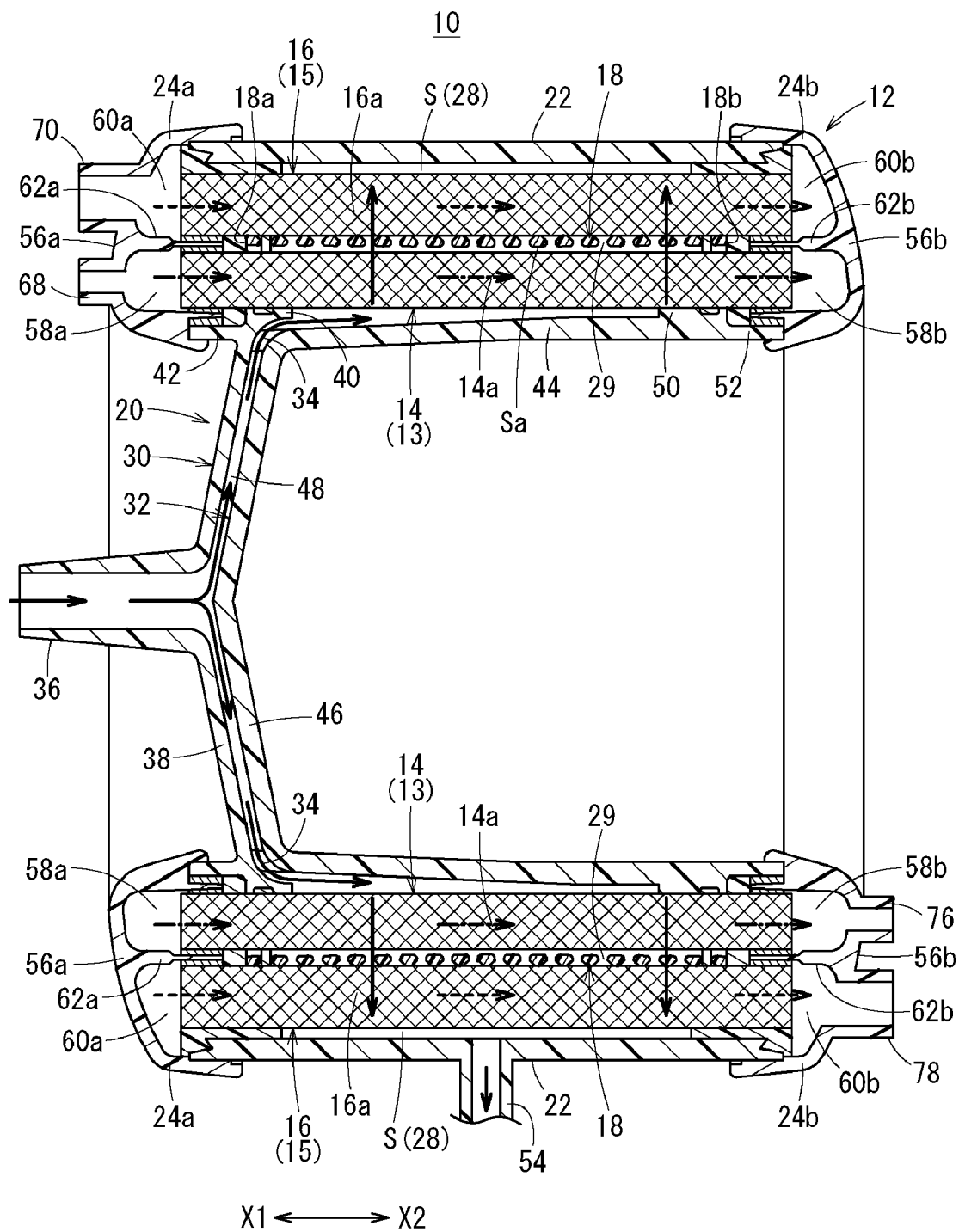
FIG. 7 is an explanatory sectional view illustrating flow of a fluid in an oxygenator.

As illustrated in FIG. 7, in the oxygenator 10, the heat medium is supplied to the heat medium inflow portion 68, oxygen gas is supplied to the gas inflow portion 70, and blood of a human body is guided to the blood inflow portion 36 by a centrifugal pump (not illustrated). The heat medium is introduced from the heat medium inflow portion 68 into the lumen of each first hollow fiber membrane 14a of the heat exchange unit 14 via the first heat medium flow path 58a. Oxygen gas is introduced from the gas inflow portion 70 into the lumen of each second hollow fiber membrane 16a of the gas exchange unit 16 via the first gas flow path 60a.

Blood is guided from the blood inflow portion 36 to the blood flow path 28 (the accommodation space S) via the blood introduction path 48. The blood in the blood flow path 28 flows through the gap between the adjacent first hollow fiber membranes 14a of the heat exchange unit 14 radially outward in the accommodation space S. In this manner, heat exchange between the blood and the heat medium in the first hollow fiber membrane 14a is performed.

The blood subjected to the heat exchange flows through the gap between the adjacent second hollow fiber membranes 16a of the gas exchange unit 16 radially outward in the accommodation space S via the slits 29 of the intermediate spacer 18. In this manner, the oxygen gas in the second hollow fiber membrane 16a passes through the wall portion of the second hollow fiber membrane 16a and is supplied to the blood and the carbon dioxide gas in the blood passes through the wall portion of the second hollow fiber membrane 16a and is removed into the second hollow fiber membrane 16a. The blood subjected to the gas exchange flows in the blood flow path 28 in the circumferential direction, flows out from the blood outflow portion 54 to the outside of the oxygenator 10, and is returned to the human body.

The heat medium subjected to the heat exchange with the blood flows out from the lumen of each first hollow fiber membrane 14a to the outside via the second heat medium flow path 58b and the heat medium outflow portion 76. The carbon dioxide gas in the lumen of each second hollow fiber membrane 16a flows to the outside via the second gas flow path 60b and the gas outflow portion 78.

Next, a method for manufacturing the oxygenator 10 will be described.

Figure 8:
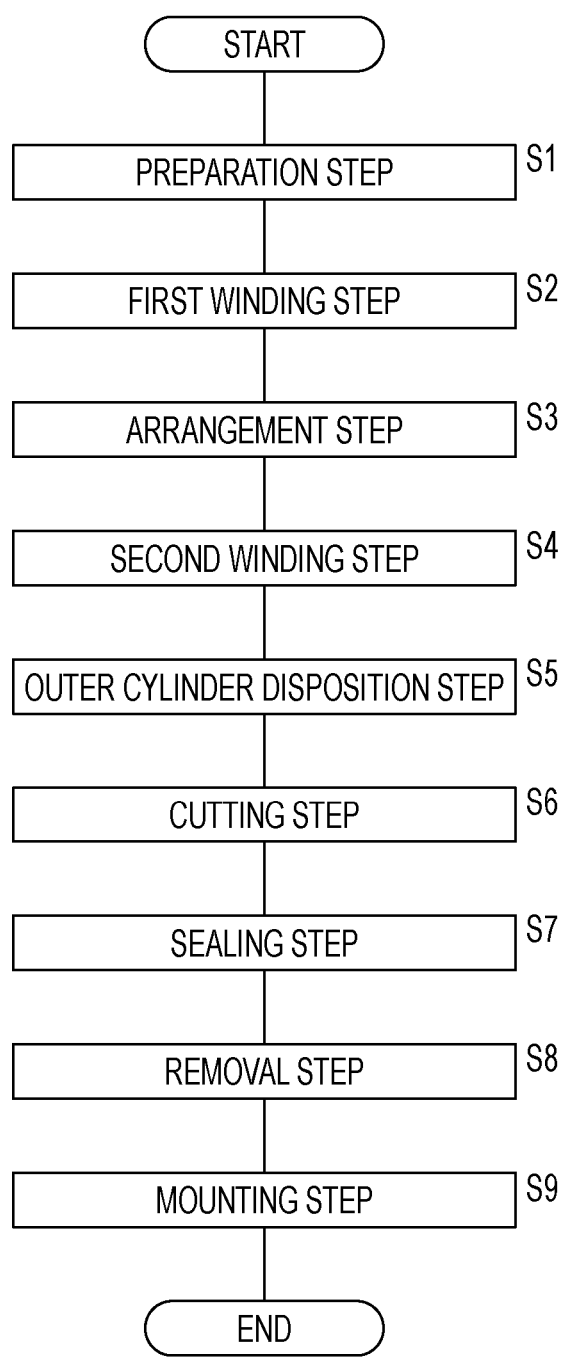
FIG. 8 is a flowchart for explanation of a method for manufacturing the oxygenator illustrated in FIG. 1.
Figure 9A:
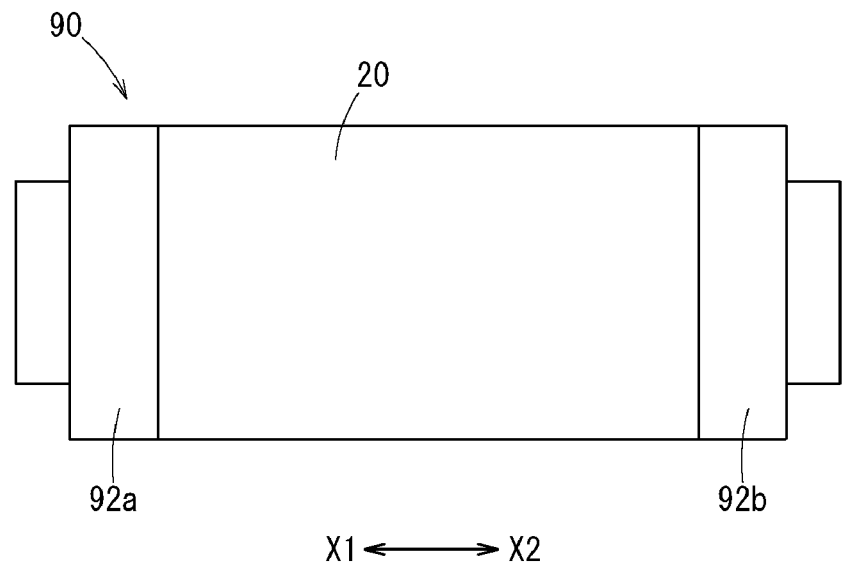
FIG. 9A is an explanatory view of a preparation step and FIG. 9B is an explanatory view of a first winding step.

In the case of manufacturing the oxygenator 10, the preparation step (step S1) in FIG. 8 is performed. In the preparation step, a core member 90 is prepared as illustrated in FIG. 9A. The core member 90 includes the core 20 described above, an annular first cap member 92a mounted on one end of the core 20, and an annular second cap member 92b mounted on the other end of the core 20. The first cap member 92a is fitted to the first annular convex portion 42, and the second cap member 92b is fitted to the second annular convex portion 52 (see FIG. 10).

Figure 9B:
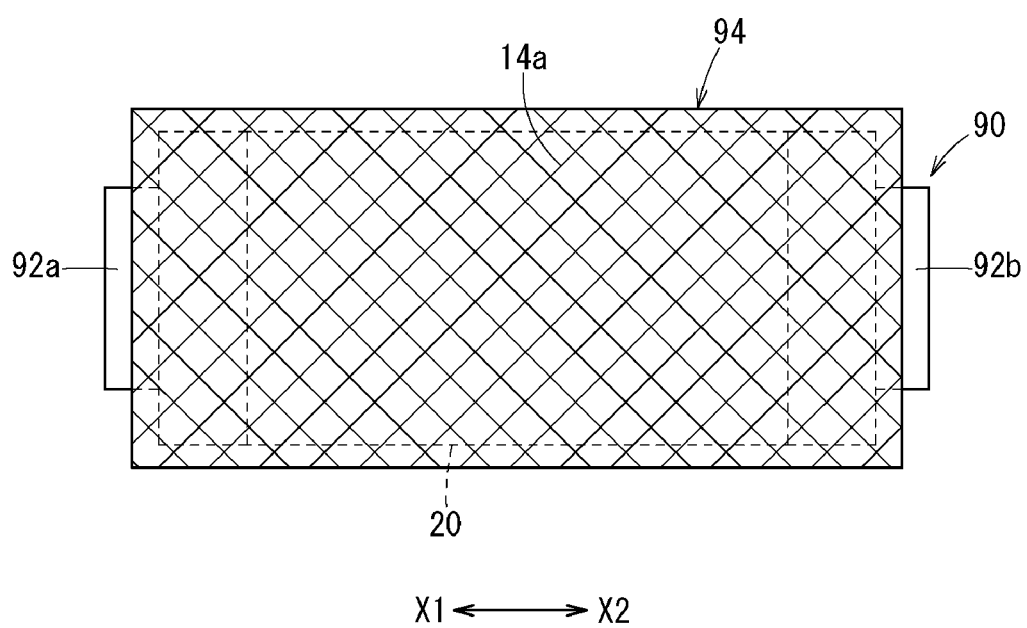
Figure 10:
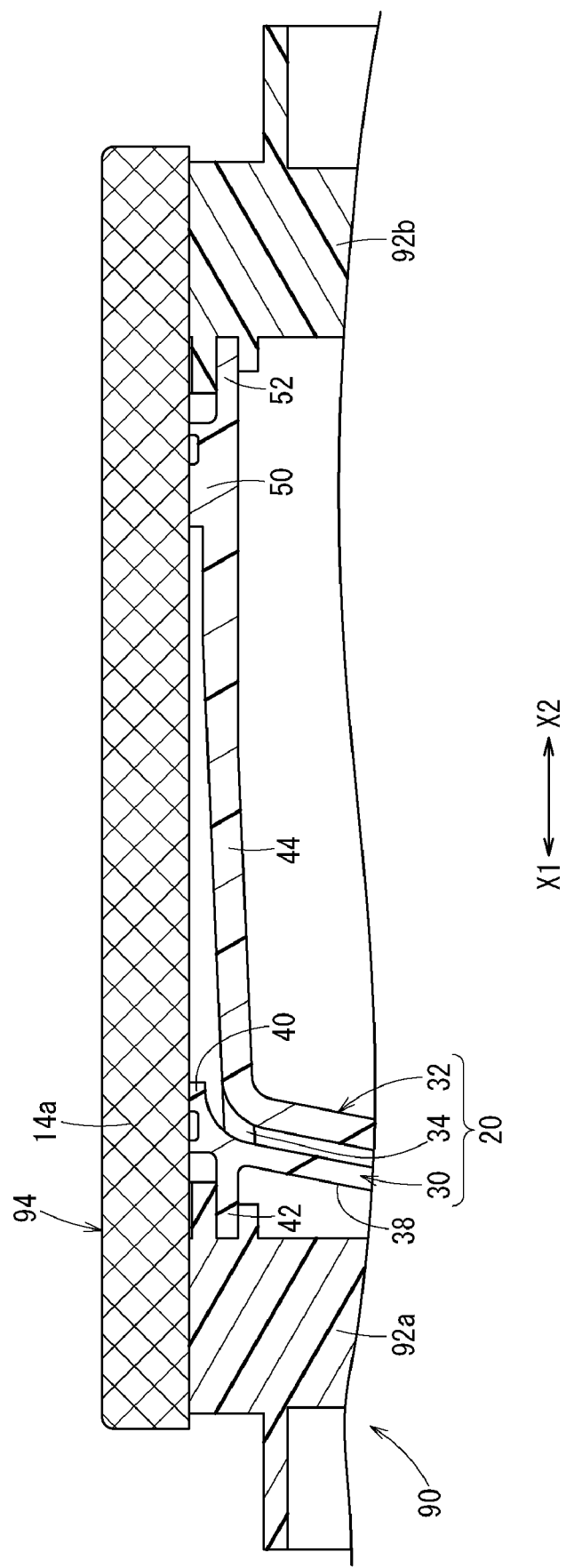
FIG. 10 is a partially omitted longitudinal sectional explanatory view of FIG. 9B.

Subsequently, as illustrated in FIGS. 8, 9B, and 10, a first cylindrical unit 94 is formed by winding the first hollow fiber membrane 14a around the outer peripheral surface of the core member 90 in the first winding step (step S2). Specifically, the first cylindrical unit 94 is formed by winding one continuous first hollow fiber membrane 14a circumferentially around the outer peripheral surface of the core member 90 and reciprocating the first hollow fiber membrane 14a plural times in the axial direction. At this time, the first hollow fiber membrane 14a is also wound around the outer peripheral surfaces of the first cap member 92a and the second cap member 92b.

Figure 11:
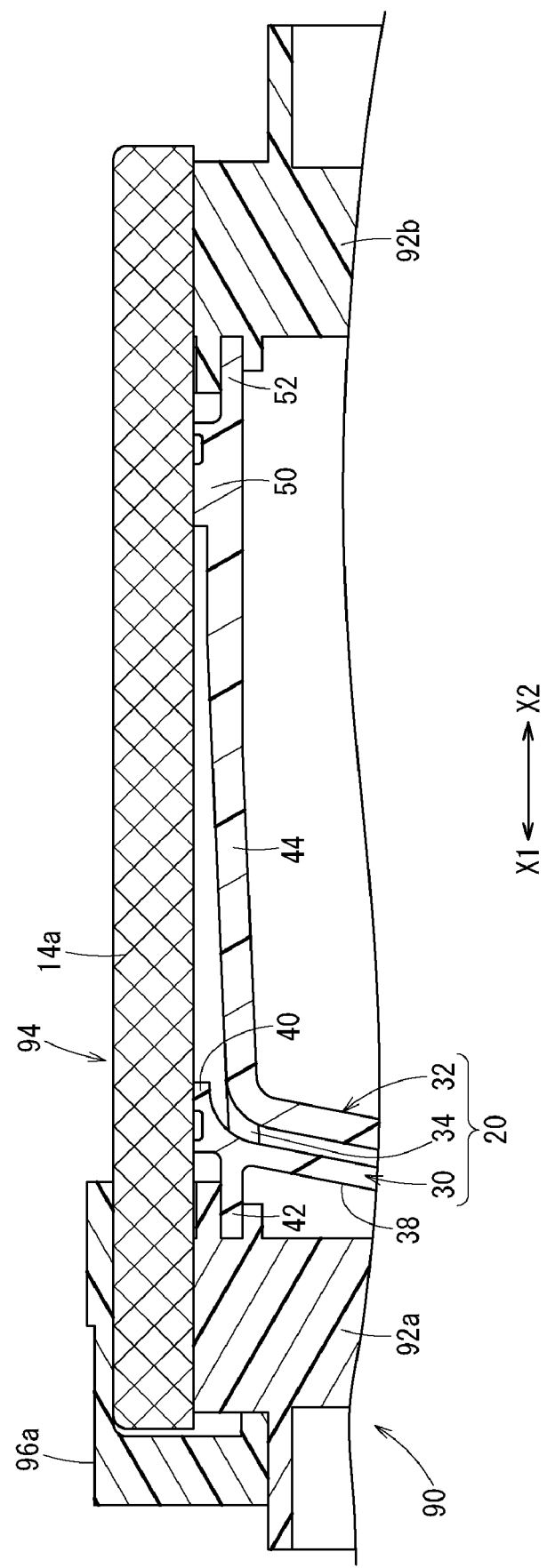
FIG. 11 is a first explanatory view of an arrangement step.
Figure 12:
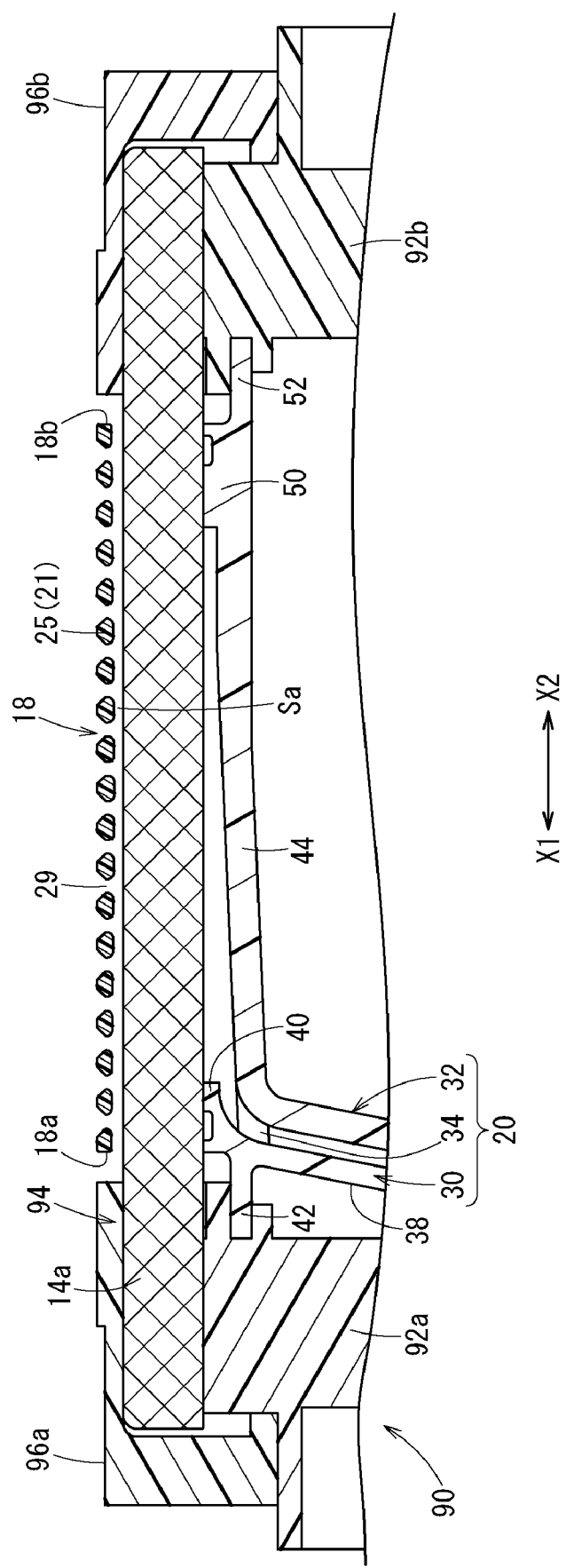
FIG. 12 is a second explanatory view of an arrangement step.

Next, the arrangement step (step S3) in FIG. 8 is performed. In the arrangement step, the first annular member 96a is disposed so as to cover only one end portion of the outer peripheral surface of the first cylindrical unit 94 as illustrated in FIG. 11. The first annular member 96a is mounted on the first cap member 92a. Moreover, the intermediate spacer 18 which is a resin molded product is arranged at the central part of the outer peripheral surface of the first cylindrical unit 94 as illustrated in FIG. 12. At this time, the intermediate spacer 18 is disposed so that the first end portion 18a is located radially outward from the first support portion 40 and the second end portion 18b is located radially outward from the second support portion 50.

The intermediate spacer 18 is arranged on the outer peripheral surface of the first cylindrical unit 94 by disposing the two divided (semi-cylindrical) spacers 23 so as to cover the central portion of the outer peripheral surface of the first cylindrical unit 94 and mounting the claw portions 33 (see FIG. 4) of these divided spacers 23 on each other. At this time, the protrusion 31 of the intermediate spacer 18 is inserted into the gap between the first hollow fiber membranes 14a adjacent to each other of the heat exchange unit 14. In this manner, the intermediate spacer 18 can be kept in a state in which the gap Sa is formed between the inner peripheral surface of the intermediate spacer 18 and the outer peripheral surface of the inner cylinder unit 13 (heat exchange unit 14) (namely, a state in which a majority of the inner peripheral surface of the intermediate spacer 18 floats from the heat exchange unit 14).

After that, a second annular member 96b is disposed so as to cover only the other end portion of the outer peripheral surface of the first cylindrical unit 94. The second annular member 96b is mounted on the second cap member 92b. In this manner, the intermediate spacer 18 is located between the first annular member 96a and the second annular member 96b.

Figure 13:
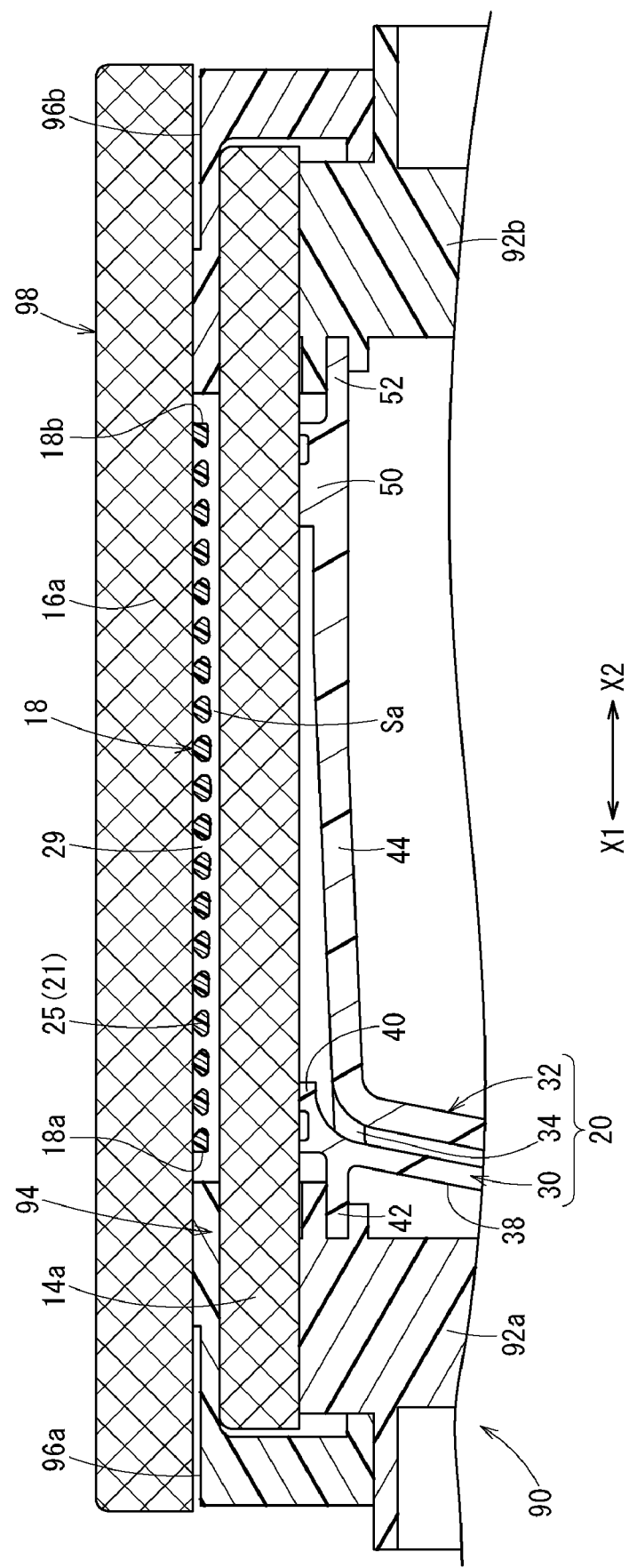
FIG. 13 is an explanatory view of a second winding step.

Subsequently, as illustrated in FIGS. 8 and 13, a second cylindrical unit 98 is formed by winding the second hollow fiber membrane 16a around the outer peripheral surfaces of the first annular member 96a, the intermediate spacer 18, and the second annular member 96b in the second winding step (step S4). Specifically, the second cylindrical unit 98 is formed by continuously winding one continuous second hollow fiber membrane 16a circumferentially around the outer peripheral surfaces of the first annular member 96a, the intermediate spacer 18, and the second annular member 96b and reciprocating the second hollow fiber membrane 16a plural times in the axial direction. Incidentally, the second hollow fiber membrane 16a is linked to the first hollow fiber membrane 14a. In other words, the first cylindrical unit 94 and the second cylindrical unit 98 are formed by one hollow fiber membrane at this step in the method.

In the second winding step, the rigid intermediate spacer 18 receives the tightening force of the second hollow fiber membrane 16a. For this reason, the first hollow fiber membrane 14a is not pressed radially inward by the winding of the second hollow fiber membrane 16a. In other words, the lumen of the first hollow fiber membrane 14a cannot become collapsed by the winding of the second hollow fiber membrane 16a.

Figure 14:
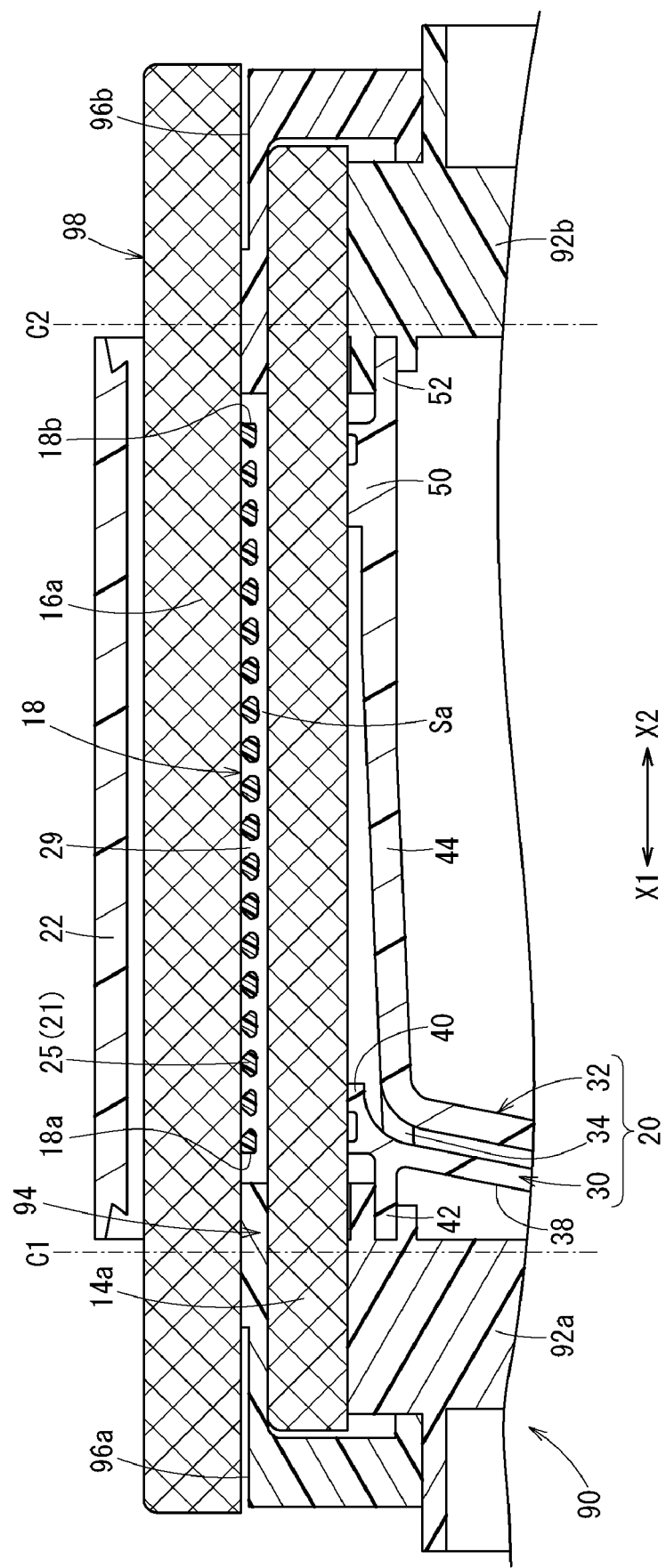
FIG. 14 is an explanatory view of an outer cylinder disposition step.
Figure 15:
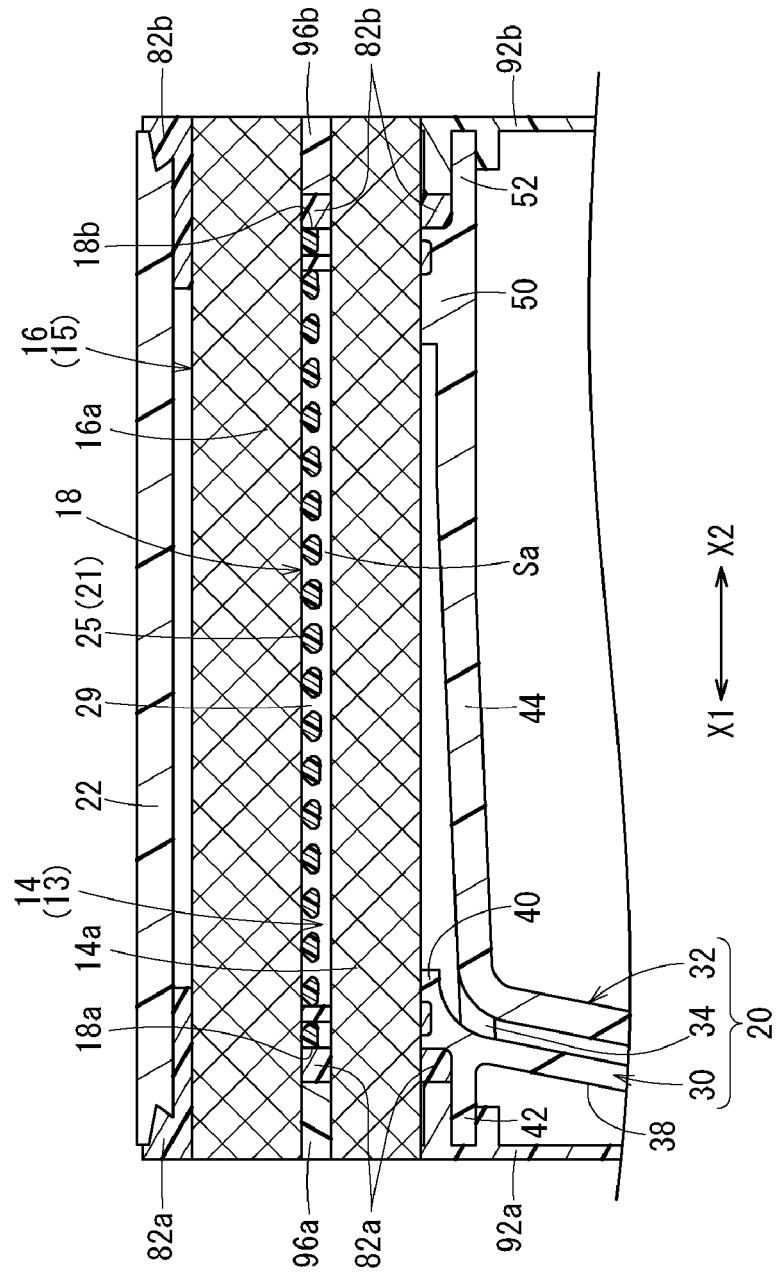
FIG. 15 is an explanatory view of a cutting step and a sealing step.

Next, as illustrated in FIGS. 8 and 14, the outer cylinder 22 is disposed so as to cover the outer surface of the second cylindrical unit 98 in the outer cylinder disposition step (step S5). Moreover, as illustrated in FIGS. 8 and 15, the heat exchange unit 14 (the inner cylinder unit 13) and the gas exchange unit 16 (the outer cylinder unit 15) are formed by cutting both end portions of the first cylindrical unit 94 and the second cylindrical unit 98 along the first cutting line C1 (see FIG. 14) and the second cutting line C2 (see FIG. 14) in the cutting step (step S6).

At this time, a part of each of the first cap member 92a, the first annular member 96a, the second cap member 92b, and the second annular member 96b is also cut off. In this manner, a part of the first cap member 92a is left between the heat exchange unit 14 and the first annular convex portion 42 and a part of the first annular member 96a is left between one end portions of the heat exchange unit 14 and the gas exchange unit 16. In addition, a part of the second cap member 92b is left between the heat exchange unit 14 and the second annular convex portion 52 and a part of the second annular member 96b is left between the other end portions of the heat exchange unit 14 and the gas exchange unit 16.

Moreover, in the sealing step (step S7), the outer sides of the first hollow fiber membrane 14a and the second hollow fiber membrane 16a at one end portions of the heat exchange unit 14 and the gas exchange unit 16 are sealed with the first sealing member 82a and the outer sides of the first hollow fiber membrane 14a and the second hollow fiber membrane 16a at the other end portions of the heat exchange unit 14 and the gas exchange unit 16 are sealed with the second sealing member 82b.

Specifically, the first sealing member 82a is injected into the outer sides of the first hollow fiber membrane 14a and the second hollow fiber membrane 16a at one end portions of the heat exchange unit 14 and the gas exchange unit 16. Thereafter, the heat exchange unit 14, the gas exchange unit 16, and the like are rotated so that the centrifugal force in the arrow X2 direction is applied to the first sealing member 82a. At this time, a cover member (not illustrated) is mounted on the end portions of the heat exchange unit 14 and the gas exchange unit 16 in the arrow X2 direction. In this manner, the first sealing member 82a spreads from one ends of the heat exchange unit 14 and the gas exchange unit 16 in the arrow X2 direction.

After the adding of the first sealing member 82a is terminated, the second sealing member 82b is injected into the outer sides of the first hollow fiber membrane 14a and the second hollow fiber membrane 16a at the other end portions of the heat exchange unit 14 and the gas exchange unit 16. Thereafter, the heat exchange unit 14, the gas exchange unit 16, and the like are rotated so that the centrifugal force in the arrow X1 direction is applied to the second sealing member 82b. At this time, a cover member (not illustrated) is mounted on the end portions of the heat exchange unit 14 and the gas exchange unit 16 in the arrow X1 direction. In this manner, the second sealing member 82b spreads from the other ends of the heat exchange unit 14 and the gas exchange unit 16 in the arrow X1 direction.

In the sealing step, the protrusion 31 of the intermediate spacer 18 is disposed between the first hollow fiber membranes 14a adjacent to each other when the heat exchange unit 14, the gas exchange unit 16, and the like are rotated. For this reason, the intermediate spacer 18 is not displaced in the axial direction with respect to the heat exchange unit 14 and the gas exchange unit 16 by the centrifugal force.

Figure 16:
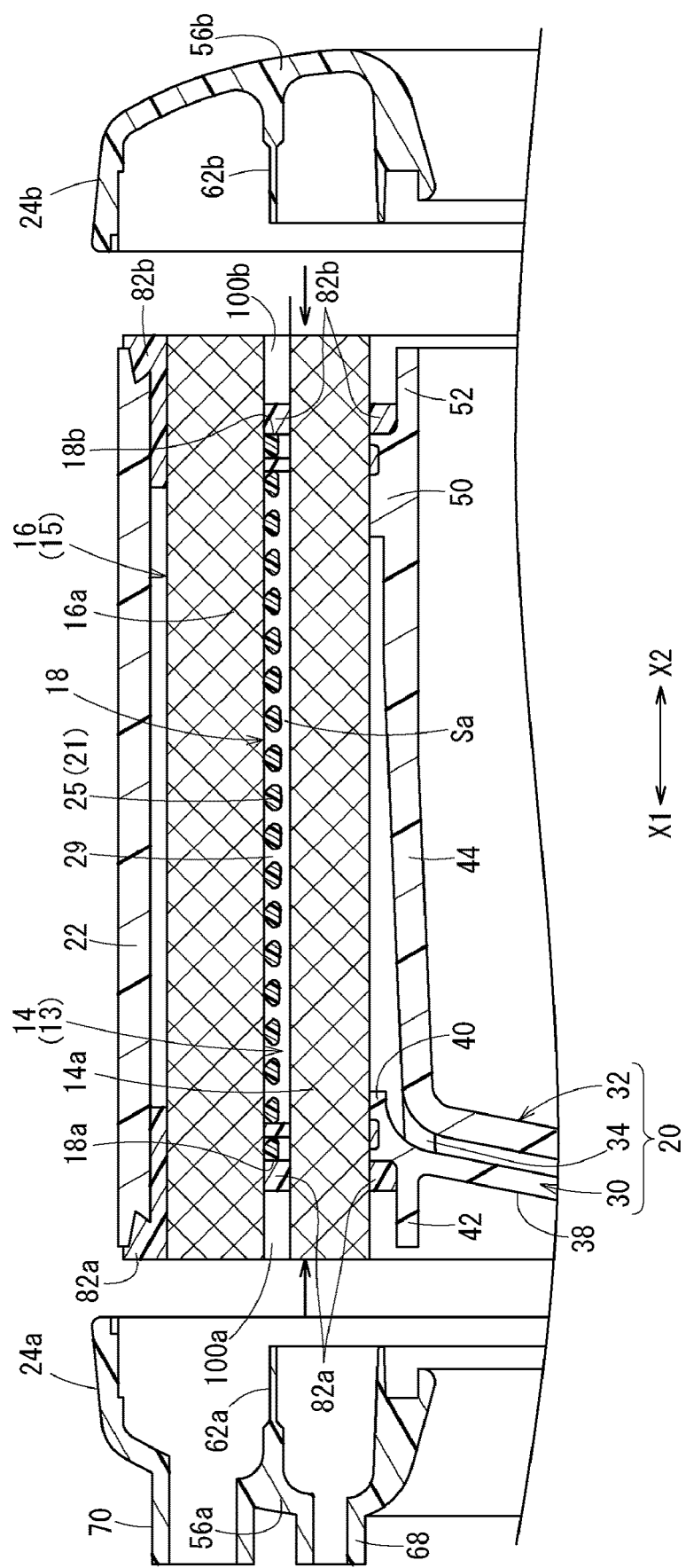
FIG. 16 is an explanatory view of a removal step and a mounting step.

Thereafter, as illustrated in FIGS. 8 and 16, the first cap member 92a, the first annular member 96a, the second cap member 92b, and the second annular member 96b are removed in the removal step (step S8). In this manner, a first gap 100a is formed between one end portions of the heat exchange unit 14 and the gas exchange unit 16 and a second gap 100b is formed between the other end portions of the heat exchange unit 14 and the gas exchange unit 16.

Moreover, in the mounting step (step S9), the first cover member 24a is fixed with the adhesive 64a in the state of being mounted on one end portions of the outer cylinder 22 and the core 20 and the second cover member 24b is fixed with the adhesive 64b in the state of being mounted on the other end portions of the outer cylinder 22 and the core 20. At this time, the protruding end portion of the first partition section 62a is inserted into the first gap 100a and the protruding end portion of the second partition section 62b is inserted into the second gap 100b. In this manner, the oxygenator 10 illustrated in FIG. 1 is manufactured.

Next, the effects of the present embodiment will be described below.

As illustrated in FIGS. 1 and 2, in the oxygenator 10, the first partition section 62a is inserted between one end portions of the heat exchange unit 14 which is the inner cylinder unit 13 and the gas exchange unit 16 which is the outer cylinder unit 15. The second partition section 62b is inserted between the other end portions of the heat exchange unit 14 and the gas exchange unit 16. The intermediate spacer 18 formed in a cylindrical shape is arranged between the heat exchange unit 14 and the gas exchange unit 16. The first end portion 18a of the intermediate spacer 18 is located at the part which does not overlap the first partition section 62a in the radial direction in one end portions of the heat exchange unit 14 and the gas exchange unit 16.

In this manner, it is possible to form the first gap 100a, into which the protruding end of the first partition section 62a can be inserted, between one end portions of the heat exchange unit 14 and the gas exchange unit 16 by the intermediate spacer 18. Hence, one end portion of the heat exchange unit 14 and one end portion of the gas exchange unit 16 are pushed (i.e., supported) in the radial direction by the first partition section 62a and it is possible to suppress the lumen of the first hollow fiber membrane 14a and the lumen of the second hollow fiber membrane 16a from being collapsed. Consequently, it is possible to suppress decreases in the heat exchange rate and the gas exchange rate.

The second end portion 18b of the intermediate spacer 18 is located at the part which does not overlap the second partition section 62b in the radial direction in the other end portions of the heat exchange unit 14 and the gas exchange unit 16. In this manner, it is possible to form the second gap 100b, into which the protruding end of the second partition section 62b can be inserted, between the other end portions of the heat exchange unit 14 and the gas exchange unit 16 by the intermediate spacer 18. Hence, the other end portion of the heat exchange unit 14 and the other end portion of the gas exchange unit 16 are pushed (i.e., supported) in the radial direction by the second partition section 62b and it is possible to suppress the lumen of the first hollow fiber membrane 14a and the lumen of the second hollow fiber membrane 16a from being collapsed. Consequently, it is possible to further suppress decreases in the heat exchange rate and the gas exchange rate.

The intermediate spacer 18 is configured to be able to independently support the gas exchange unit 16 in a state in which the gap Sa is formed between the inner peripheral surface of the intermediate spacer 18 and the outer peripheral surface of the inner cylinder unit 13 (heat exchange unit 14). In this manner, the tightening force of the second hollow fiber membrane 16a can be effectively received by the intermediate spacer 18 (without resort to the heat exchange unit 14). Hence, it is possible to prevent the lumen of the first hollow fiber membrane 14a from being collapsed by the tightening force of the second hollow fiber membrane 16a.

The thickness of the part inserted between the end portions of the heat exchange unit 14 and the gas exchange unit 16 (radial thickness of the protruding end portion) of each of the first partition section 62a and the second partition section 62b is thinner than the wall thickness of the intermediate spacer 18. In this manner, it is possible to further prevent the lumen of the first hollow fiber membrane 14a and the lumen of the second hollow fiber membrane 16a from being collapsed by the first partition section 62a and the second partition section 62b.

The intermediate spacer 18 has the plurality of annular portions 21 which is arranged in the axial direction and extend in the circumferential direction and the connection portion 27 which connects the annular portions 21 adjacent to each other in the axial direction to each other. The slit 29 as the blood flow path 28 is formed between the annular portions 21 adjacent to each other. In this manner, it is possible to effectively improve the rigidity of the intermediate spacer 18 in the radial direction. Hence, the tightening force of the second hollow fiber membrane 16a can be reliably received by the intermediate spacer 18.

A plurality of connection portions 27 is provided in the circumferential direction of the intermediate spacer 18. For this reason, it is possible to more effectively improve the rigidity of the intermediate spacer 18 in the radial direction.

The annular portion 21 (the peripheral wall portion 25) is formed so that the thickness along the axial direction decreases radially outward. In this manner, it is possible to decrease the contact area between the second hollow fiber membrane 16a and the intermediate spacer 18 and thus to efficiently bring blood into contact with the second hollow fiber membrane 16a.

The protrusion 31 which suppresses movement of the intermediate spacer 18 in the axial direction with respect to the heat exchange unit 14 by coming into contact with the heat exchange unit 14 and forms the gap Sa between the inner peripheral surface of the intermediate spacer 18 and the outer peripheral surface of the inner cylinder unit 13 (heat exchange unit 14) is provided on the inner surface of the intermediate spacer 18. In this manner, it is possible not only to suppress the displacement of the intermediate spacer 18 in the axial direction with respect to the heat exchange unit 14 and the gas exchange unit 16 by the protrusion 31 but also to effectively prevent the lumen of the first hollow fiber membrane 14a of the inner cylinder unit 13 (heat exchange unit 14) from being collapsed by preventing the transmission of the tightening force of the second hollow fiber membrane 16a to the first hollow fiber membrane 14a.

The protruding length L of the protrusion 31 is equal to or less than the outer diameter of the first hollow fiber membrane 14a. For this reason, it is possible to locate the protrusion 31 between the first hollow fiber membranes 14a adjacent to each other (e.g., different winding loops of heat exchange unit 14). In this manner, it is possible to effectively suppress the displacement of the intermediate spacer 18 in the axial direction with respect to the heat exchange unit 14.

The protrusion 31 is formed so that the dimension along the axial direction decreases radially inward. In this manner, it is possible to efficiently locate the tip portion of the protrusion 31 between different winding loops of the first hollow fiber membranes 14a adjacent to each other.

The protrusion 31 is located at a site of the inner surface of the annular portion 21 (the peripheral wall portion 25), the site being adjacent to the connection portion 27. For this reason, it is possible to dispose the protrusion 31 at the part having a relatively large area of the inner surface of the intermediate spacer 18 and thus to improve the rigidity of the protrusion 31.

In the method for manufacturing the oxygenator 10, the intermediate spacer 18 is arranged on the outer surface of the first cylindrical unit 94 so that the first gap 100a is formed between one end portions of the heat exchange unit 14 and the gas exchange unit 16 and the second gap 100b is formed between the other end portions of the heat exchange unit 14 and the gas exchange unit 16 at the time of the mounting step in the arrangement step. Moreover, in the mounting step, the first partition section 62a is inserted into the first gap 100a and the second partition section 62b is inserted into the second gap 100b. In this manner, it is possible to avoid decreases in the heat exchange rate and the gas exchange rate of the oxygenator 10.

In the arrangement step, the first annular member 96a is disposed so as to cover only one end portion of the first cylindrical unit 94 and the second annular member 96b is disposed so as to cover only the other end portion of the first cylindrical unit 94. In the second winding step, the second hollow fiber membrane 16a is wound around the outer surface of each of the intermediate spacer 18, the first annular member 96a, and the second annular member 96b.

Moreover, the removal step of removing the first annular member 96a and the second annular member 96b is performed after the sealing step.

In this manner, it is possible to reliably form the first gap 100a, into which the first partition section 62a can be inserted, between one end portions of the heat exchange unit 14 and the gas exchange unit 16 by the first annular member 96a. In addition, it is possible to reliably form the second gap 100b, into which the second partition section 62b can be inserted, between the other end portions of the heat exchange unit 14 and the gas exchange unit 16 by the second annular member 96b.

In the first winding step, the first cylindrical unit 94 is formed by winding one continuous first hollow fiber membrane 14a and reciprocating the first hollow fiber membrane 14a plural times in the axial direction. In this manner, it is possible to efficiently form the first cylindrical unit 94. In the second winding step, the second cylindrical unit 98 is formed by winding one continuous second hollow fiber membrane 16a and reciprocating the second hollow fiber membrane 16a plural times in the axial direction. In this manner, it is possible to efficiently form the second cylindrical unit 98.

In the oxygenator 10, the first end portion 18a of the intermediate spacer 18 may be located at a region which does not overlap the first partition section 62a in the radial direction in one end portions of the heat exchange unit 14 and the gas exchange unit 16 and the second end portion 18b may be located at a region (for example, the central portion in the axial direction) which is not the other end portions of the heat exchange unit 14 and the gas exchange unit 16. Even in this case, it is possible to prevent the lumen of the first hollow fiber membrane 14a and the lumen of the second hollow fiber membrane 16a from being collapsed by the first partition section 62a at one end portions of the heat exchange unit 14 and the gas exchange unit 16.

In some embodiments of the oxygenator 10, the heat exchange unit 14 may be configured as the outer cylinder unit 15 and the gas exchange unit 16 may be configured as the inner cylinder unit 13.

In addition, in the oxygenator 10, the first end portion 18a of the intermediate spacer 18 may be located at a region (for example, the central portion in the axial direction) which is not one end portions of the heat exchange unit 14 and the gas exchange unit 16 and the second end portion 18b may be located at a region which does not overlap the second partition section 62b in the radial direction in the other end portions of the heat exchange unit 14 and the gas exchange unit 16.

In some embodiments of the method for manufacturing the oxygenator 10, the first annular member 96a and the second annular member 96b may not be provided on the outer surface of the first cylindrical unit 94 in the arrangement step. Even in this case, it is possible to form the first gap 100a and the second gap 100b by the intermediate spacer 18.

The oxygenator and the method for manufacturing the same according to the present invention are not limited to the above-described embodiments and may employ various configurations without departing from the gist of the present invention.

What is claimed is:
1. An oxygenator, comprising:
a housing comprising a core, an outer housing cylinder, and first and second cover members attached to end portions of the core and the outer housing cylinder;
an inner wound cylinder unit configured as one of a heat exchange unit or a gas exchange unit by winding a first hollow fiber membrane;
an outer wound cylinder unit configured as the other of the heat exchange unit or the gas exchange unit by winding a second hollow fiber membrane, wherein the inner and outer wound cylinders are accommodated in the housing overlapping each other in a radial direction so that a blood flow path is formed on an outer side of the first hollow fiber membrane and an outer side of the second hollow fiber membrane; and
a cylindrical intermediate spacer arranged between the inner wound cylinder unit and the outer wound cylinder unit;
wherein the housing includes a pair of partition sections extending axially from the first and second cover members that partitions each of spaces on both sides in an axial direction from the inner wound cylinder unit and the outer wound cylinder unit into a heat medium flow path and a gas flow path, and wherein the partition sections are each inserted between end portions of the inner wound cylinder unit and the outer wound cylinder unit;
wherein at least one end portion of the intermediate spacer is located at a region that does not overlap the partition section in a radial direction in end portions of the inner wound cylinder unit and the outer wound cylinder unit; and
wherein the intermediate spacer is configured to independently support the outer wound cylinder unit in a state in which a gap is formed between an inner peripheral surface of the intermediate spacer and an outer peripheral surface of the inner wound cylinder unit.

2. The oxygenator according to claim 1, wherein:
a radial thickness of a protruding end of the partition section inserted between end portions of the inner wound cylinder unit and the outer wound cylinder unit is thinner than a radial wall thickness of the intermediate spacer.

3. An oxygenator, comprising:
a housing;
an inner cylinder unit configured as one of a heat exchange unit or a gas exchange unit by winding a first hollow fiber membrane;
an outer cylinder unit configured as the other of the heat exchange unit or the gas exchange unit by winding a second hollow fiber membrane, wherein the inner and outer cylinders are accommodated in the housing overlapping each other in a radial direction so that a blood flow path is formed on an outer side of the first hollow fiber membrane and an outer side of the second hollow fiber membrane; and
a cylindrical intermediate spacer arranged between the inner cylinder unit and the outer cylinder unit;
wherein the housing includes a pair of partition sections that partitions each of spaces on both sides in an axial direction from the inner cylinder unit and the outer cylinder unit into a heat medium flow path and a gas flow path, and wherein the partition sections are each inserted between end portions of the inner cylinder unit and the outer cylinder unit;
wherein at least one end portion of the intermediate spacer is located at a region that does not overlap the partition section in a radial direction in end portions of the inner cylinder unit and the outer cylinder unit;
wherein the intermediate spacer is configured to independently support the outer cylinder unit in a state in which a gap is formed between an inner peripheral surface of the intermediate spacer and an outer peripheral surface of the inner cylinder unit; and wherein the intermediate spacer is comprised of:
- a plurality of annular portions arranged in the axial direction and extend in a circumferential direction; and
- a connection portion that connects the annular portions adjacent to each other in the axial direction to each other;
- wherein a slit is disposed between the annular portions adjacent to each other forming a portion of the blood flow path.

4. The oxygenator according to claim 3 wherein:
the annular portions are each formed so that a thickness along the axial direction decreases radially outward.

5. The oxygenator according to claim 3, wherein the intermediate spacer further comprises:
a protrusion is provided on an inner surface of the intermediate spacer that prevents movement of the intermediate spacer in the axial direction with respect to the inner cylinder unit by coming into contact with the inner cylinder unit and forms a gap between an inner peripheral surface of the intermediate spacer and an outer peripheral surface of the inner cylinder unit.

6. The oxygenator according to claim 5, wherein:
a protruding length of the protrusion is equal to or less than an outer diameter of the first hollow fiber membrane.

7. The oxygenator according to claim 5 wherein:
the protrusion is formed so that a dimension along the axial direction decreases radially inward.

8. The oxygenator according to claim 5, comprising a plurality of protrusions, wherein:
each respective protrusion is located at a respective site of an inner surface of each of the annular portions, each respective site being adjacent to a respective connection portion.

9. The oxygenator according to claim 1, wherein:
each end portion of the intermediate spacer is located at a region that does not overlap the partition section in a radial direction in end portions of the inner wound cylinder unit and the outer wound cylinder unit.

10. A method for manufacturing an oxygenator including an inner wound cylinder unit configured as one of a heat exchange unit or a gas exchange unit and an outer wound cylinder unit configured as the other of the heat exchange unit or the gas exchange unit that are disposed to overlap each other in a radial direction, the method comprising the steps of:
- a first winding step of forming the inner wound cylinder unit by winding a first hollow fiber membrane on an outer surface of a core;
- an arrangement step of arranging a cylindrical intermediate spacer on an outer surface of the inner wound cylinder unit;
- a second winding step of forming the outer wound cylinder unit by winding a second hollow fiber membrane around an outer surface of the intermediate spacer;
- an outer housing cylinder disposition step of disposing an outer housing cylinder so as to cover an outer surface of the outer wound cylinder unit;
- a cutting step comprised of cutting both end portions of the inner wound cylinder unit and the outer wound cylinder unit;
- a sealing step of sealing outer sides of the first hollow fiber membrane and the second hollow fiber membrane at both end portions of the inner wound cylinder unit and the outer wound cylinder unit with a sealing member; and
- a mounting step of mounting cover members on both end portions of the core and the outer housing cylinder and forming a heat medium flow path and a gas flow path in the respective cover members;

wherein the intermediate spacer is configured to independently support the outer wound cylinder unit in a state in which a gap is formed between an inner peripheral surface of the intermediate spacer and an outer peripheral surface of the inner wound cylinder unit;

wherein the intermediate spacer is arranged on an outer surface of the inner wound cylinder unit so that a gap is formed at least between one end portions of the inner wound cylinder unit and the outer wound cylinder unit or between the other end portions of the inner wound cylinder unit and the outer wound cylinder unit when performing the mounting step in the arrangement step; and wherein a partition section of the cover member is inserted into the gap formed by the intermediate spacer in the mounting step;

wherein the intermediate spacer is comprised of an annular member which is arranged so as to cover only both end portions of the inner wound cylinder unit in the arrangement step;

wherein the second hollow fiber membrane is wound around an outer surface of each of the intermediate spacer and the annular member in the second winding step; and wherein the method further comprises a removal step of removing the annular member after the sealing step.

11. The method for manufacturing an oxygenator according to claim 10, wherein:
the intermediate spacer is arranged by disposing a plurality of divided semi-cylindrical spacers divided in a circumferential direction on an outer surface of the inner wound cylinder unit and connecting the divided spacers to each other in the arrangement step.

12. The method for manufacturing an oxygenator according to claim 10, wherein:
the intermediate spacer is arranged on an outer surface of the inner wound cylinder unit so that the gap is formed between one end portions of the inner wound cylinder unit and the outer wound cylinder unit and between the other end portions of the inner wound cylinder unit and the outer wound cylinder unit when performing the mounting step in the arrangement step; and
the partition section of each of the cover members is inserted into each of the gaps formed by the intermediate spacer in the mounting step.

13. The method for manufacturing an oxygenator according to claim 10:
wherein the inner wound cylinder unit is formed by winding one continuous first hollow fiber membrane around an outer surface of the core and reciprocating the one continuous first hollow fiber membrane a plurality of times in an axial direction in the first winding step; and
wherein the outer wound cylinder unit is formed by winding one continuous second hollow fiber membrane around an outer surface of the intermediate spacer and reciprocating the one continuous second hollow fiber membrane a plurality of times in the axial direction in the second winding step.

14. The oxygenator according to claim 3, wherein:
a plurality of connection portions are spaced apart in the circumferential direction of the intermediate spacer.

* * * * *